(12) United States Patent
Cristalli

(10) Patent No.: US 7,189,730 B2
(45) Date of Patent: Mar. 13, 2007

(54) A$_{2A}$ ADENOSINE RECEPTOR ANTAGONISTS

(75) Inventor: Gloria Cristalli, Camerino (IT)

(73) Assignee: CV Therapeutics, Inc., Palo Alto, CA (US)

( * ) Notice: Subject to any disclaimer, the term of this patent is extended or adjusted under 35 U.S.C. 154(b) by 503 days.

(21) Appl. No.: 10/322,985

(22) Filed: Dec. 18, 2002

(65) Prior Publication Data
US 2003/0149060 A1 Aug. 7, 2003

Related U.S. Application Data

(60) Provisional application No. 60/342,455, filed on Dec. 18, 2001.

(51) Int. Cl.
C07D 473/40 (2006.01)
C07D 473/16 (2006.01)
C07D 473/24 (2006.01)
C07D 31/52 (2006.01)
C07D 31/522 (2006.01)

(52) U.S. Cl. .............. 514/263.22; 544/264; 544/276; 544/277; 514/263.37; 514/263.38; 514/263.4; 514/263.23

(58) Field of Classification Search ............ 544/276, 544/277; 514/263.37, 263.38, 263.23, 263.28, 514/263.4
See application file for complete search history.

(56) References Cited

U.S. PATENT DOCUMENTS

| 5,300,509 A | | 4/1994 | Block et al. | |
| 5,500,428 A | * | 3/1996 | Block et al. | 514/263.2 |
| 6,841,549 B1 | * | 1/2005 | Asano et al. | 514/183 |
| 2003/0064999 A1 | | 4/2003 | Palle et al. | |
| 2004/0132748 A1 | * | 7/2004 | Isobe et al. | 514/263.2 |
| 2004/0204428 A1 | * | 10/2004 | Giorgio et al. | 514/263.2 |

FOREIGN PATENT DOCUMENTS

| EP | 1035123 A | 9/2000 |
| WO | WO 9805335 A | 2/1998 |
| WO | WO 0044750 A | 8/2000 |
| WO | WO 01/49688 A1 | 7/2001 |

OTHER PUBLICATIONS

Chen J et al: "A Novel and Efficient Route to Chiral 2-Substituted Carbocyclic 5'-N-Ethyl-Carboxamido-Adenosine (C-Neca)", Tetrahedron Elsevier Science Publishers, Amsterdam, NL, vol. 30, No. 41, 1989, pp. 5543-5546, XP002014505, ISSN: 0040-4020, table 1 and p. 5545, formulae 3, 4.
K.J.M. Andrews et al: "Experiments on the Synthesis of Purine Nucleosides.", Journal of the Chemical Society, 1949, pp. 2490-2497, XP002236533, Letchworth GB, p. 2491, formula (II); pp. 2495-2496.

* cited by examiner

*Primary Examiner*—Mark L. Berch
(74) *Attorney, Agent, or Firm*—Brian Lewis; Pauline Ann Clarke; J. Elin Hartrum

(57) ABSTRACT

Disclosed are novel A$_{2A}$ adenosine receptor antagonists of the formula:

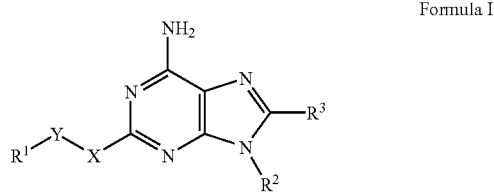

Formula I wherein:
R$^1$ is optionally substituted aryl or optionally substituted heteroaryl;
R$^2$ is optionally substituted lower alkyl or optionally substituted cycloalkyl;
R$^3$ is hydrogen, halogen, optionally substituted alkoxy, optionally substituted aryl, optionally substituted heteroaryl, or optionally substituted heterocyclyl;
X is —O—, —S—, or —NH—; and
Y is optionally substituted alkylene;
and the pharmaceutically acceptable salts thereof;
which are useful for treating various disease states, for example cardiovascular disorders, including tissue damage due to ischemia, CNS diseases, including Parkinson's disease, depression, and the like.

21 Claims, No Drawings

$A_{2A}$ ADENOSINE RECEPTOR ANTAGONISTS

FIELD OF THE INVENTION

The present invention relates to novel compounds that are $A_{2A}$ adenosine receptor antagonists, and to their use in treating mammals for various disease states, such as CNS disorders, including the "movement disorders" (Parkinson's disease, Huntington's Chorea, and catelepsy), and cerebral ischemia, excitotoxicity, cognitive and physiological disorders, depression, and the like. The invention also relates to methods for the preparation of such compounds, and to pharmaceutical compositions containing them.

BACKGROUND

Adenosine receptors are subdivided into four general subtypes; $A_1$, $A_{2A}$, $A_{2B}$, and $A_3$, all of which modulate important physiological processes ((G. L. Stiles, K. A. Jacobson, and M. F. Jarvis, Wiley-Liss: New York, (1997); pp 29–37; V. Ralevic; G. Burnstock, G. *Pharmacol. Rev.* (1998) Vol. 50, 413–492). For example, stimulation of the $A_1$ adenosine receptors shortens the duration and decreases the amplitude of the action potential of AV nodal cells, and hence prolongs the refractory period of the AV nodal cell. Thus, stimulation of $A_1$ receptors provides a method of treating supraventricular tachycardias, including termination of nodal re-entrant tachycardias, and control of ventricular rate during atrial fibrillation and flutter. Stimulation of cell surface $A_{2A}$ receptors produces dilation of the coronary resistance vessels, which phenomenon is useful for pharmacological stress imaging. $A_{2B}$ receptors have been implicated in mast cell activation, asthma, vasodilation, regulation of cell growth, intestinal function, and modulation of neurosecretion (See Adenosine $A_{2B}$ Receptors as Therapeutic Targets, Drug Dev Res 45:198; Feoktistov et al., Trends Pharmacol Sci 19:148–153). $A_3$ adenosine receptors modulate cell proliferation processes. In particular, compounds that are $A_3$ receptor agonists have utility in the therapeutic and/or prophylactic treatment of cancer, cardiac disease, infertility, kidney disease, and CNS disorders.

Recently, $A_{2A}$ receptors have been demonstrated to be involved in CNS mediated effects such as movement, and compounds that act as agonists of the $A_{2A}$ receptor produce symptoms of "movement disorders." Movement disorders are exemplified by Parkinson's Disease, which is characterized by symptoms of muscle rigidity, tremor and paucity of movement. The symptoms of Parkinson's Disease are due to the degeneration and destruction of the dopaminergic neurones in the substantia nigra, which causes a loss of dopamine, a neurotransmitter that regulates movement. The decrease in dopamine leads to a relative excess of acetylcholine, which produces the tremor associated with Parkinsons Disease. Treatment strategies, therefore, have been aimed at stimulating dopamine levels and/or inhibiting the action of acetylcholine. These treatments have not been effective in long term control of the disorder or prevention of its progression.

It has been found that compounds that antagonize the effects of adenosine at the $A_{2A}$ receptor mitigate the effect of movement disorders. For example, theophylline, which has an antagonistic effect at the $A_{2A}$ receptor, provides significant improvement of symptoms in Parkinson's patients. KF 17837, a selective adenosine $A_{2A}$ receptor antagonist, ameliorates experimentally induced cataleptic responses.

$A_{2A}$ receptor antagonists also possess neuroprotective properties. $A_{2A}$ antagonists have been shown to block kainate-induced excitotoxicity in the hippocampus, to reduce ischemia-evoked glutamate and aspartate release from the cortex, and to reduce the extent of the ischemia-induced injury in rats and gerbils. Further evidence for $A_{2A}$ receptor mediated neuroprotection arises from studies demonstrating that both cerebral infarct size and neurological deficits following transient ischemia are attenuated in $A_{2A}$ receptor knockout mice. These data are in line with the view that adenosine confers neuroprotective effects in part by inhibiting glutamate release. These findings are significant because glutamate excitotoxicity has been implicated in the pathogenesis of Parkinson's diseases, and it has been speculated that a blockade or reduction in glutamteric neurotransmission may arrest neurodegeneration in Parkinson's. Thus, $A_{2A}$ receptor antagonists have a dual role in treating Parkinson's Disease, by effectively slowing further neurodegeneration while providing symptomatic relief with fewer side effects compared to existing therapies.

As previously mentioned, stimulation of $A_{2A}$ adenosine receptors produces dilation of the coronary resistance vessels. Although this phenomenon is useful for pharmacological stress imaging, it is not favorable for patients who have elevated endogenous adenosine, because excessive vasodilation potentially leads to coronary steal. The phenomenon of coronary steal can cause tissue damage, because ischemia may be produced in the vascular beds fed by the artery that has lowered blood flow due to the more favorable vasodilation of healthy adjoining arteries. Accordingly, an $A_{2A}$ antagonist will prevent the phenomenon of coronary steal.

Accordingly, it is desired to provide compounds that are potent $A_{2A}$ antagonists, useful in the treatment of various disease states related to modulation of the $A_{2A}$ receptor, in particular cardiovascular diseases such as tissue damage caused by ischemia, and CNS-related diseases such as Parkinson's Disease. Preferably, the compounds would be selective for the $A_{2A}$ receptor, thus avoiding side effects caused by interaction with other adenosine receptors.

SUMMARY OF THE INVENTION

It is an object of this invention to provide $A_{2A}$ receptor antagonists. Accordingly, in a first aspect, the invention relates to compounds of Formula I:

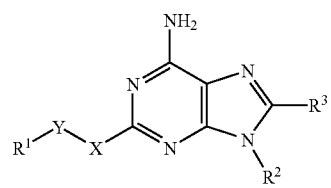

Formula I wherein:

$R^1$ is optionally substituted aryl or optionally substituted heteroaryl;

$R^2$ is optionally substituted lower alkyl or optionally substituted cycloalkyl;

$R^3$ is hydrogen, halogen, optionally substituted alkoxy, optionally substituted aryl, optionally substituted heteroaryl, or optionally substituted heterocyclyl;

with the proviso that $R^3$ cannot be pyrazolyl;

X is —O—, —S—, or —NH—; and

Y is optionally substituted alkylene.

In a second aspect, the invention relates to pharmaceutical formulations, comprising a therapeutically effective amount of a compound of Formula I and at least one pharmaceutically acceptable excipient.

A third aspect of this invention relates to a method of using the compounds of Formula I in the treatment of a disease or condition in a mammal that can be usefully treated with an $A_{2A}$ receptor antagonist, comprising administering to a mammal in need thereof a therapeutically effective dose of a compound of Formula I. Such diseases include, but are not limited to, Parkinson's disease, Huntington's Chorea, and catelepsy, and cerebral ischemia, excitotoxicity, cognitive and physiological disorders. The compounds of Formula I are also useful for the inhibition of coronary vasodilation, which treatment prevents coronary steal.

The compounds of Formula I in which $R^2$ is optionally substituted lower alkyl are preferred, particularly those in which $R^1$ is optionally substituted aryl. Within this group, a preferred class of compounds include those in which $R^3$ is hydrogen, halogen, or optionally substituted heteroaryl, particularly those in which Y is lower alkylene. Within this class, a preferred subclass of compounds are those in which X is —NH—. Within this subclass, it is preferred that Y is methylene or ethylene, and $R^2$ is methyl, ethyl, or n-propyl, particularly where $R^1$ is optionally substituted phenyl, $R^2$ is ethyl, and $R^3$ is hydrogen, bromo, or furan-2-yl.

A second preferred subclass of compounds are those in which X is —O— or —S—. Within this subclass, it is preferred that Y is methylene or ethylene, and $R^2$ is methyl, ethyl, or n-propyl, particularly where $R^1$ is optionally substituted phenyl, $R^2$ is ethyl, and $R^3$ is hydrogen or bromo.

At present, the preferred compounds include 2-benzylamino-8-bromo-9-ethyl-9H-purin-6-ylamine; 2-(2-phenylethyl)amino-8-bromo-9-ethyl-9H-purin-6-ylamine, 2-[2-(3,4-dimethoxyphenyl)ethyl]amino-8-bromo-9-ethyl-9H-purin-6-ylamine; 2-[2-(3,4-dihydroxyphenyl)ethyl]amino-8-bromo-9-ethyl-9H-purin-6-ylamine; 2-[2-(4-bromophenyl)ethyl]amino-8-bromo-9-ethyl-9H-purin-6-ylamine; 2-[2-(4-fluorophenyl)ethyl]amino-8-bromo-9-ethyl-9H-purin-6-ylamine; 2-[2-(4-hydroxyphenyl)ethyl]amino-8-bromo-9-ethyl-9H-purin-6-ylamine; 2-(2-phenylethyl)amino-8-(furan-2-yl)-9-ethyl-9H-purin-6-ylamine; 2-[2-(2-fluorophenyl)ethyl]amino-9-ethyl-9H-purin-6-ylamine; 2-(2-phenylethoxy)-8-bromo-9-ethyl-9H-purin-6-ylamine; and 2-(2-phenylethylthio)-8-bromo-9-ethyl-9H-purin-6-ylamine.

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:
1) an alkyl group as defined above, having from 1 to 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
2) an alkyl group as defined above that is interrupted by 1–5 atoms or groups independently chosen from oxygen, sulfur and —NR$_a$—, where R$_a$ is chosen from hydrogen, alkyl, cycloalkyl, alkenyl, cycloalkenyl, alkynyl, aryl, heteroaryl and heterocyclyl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
3) an alkyl group as defined above that has both from 1 to 5 substituents as defined above and is also interrupted by 1–5 atoms or groups as defined above.

The term "lower alkyl" refers to a monoradical branched or unbranched saturated hydrocarbon chain having from 1 to 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1 to 3 substituents, as defined for substituted alkyl, or a lower alkyl group as defined above that is interrupted by 1–5 atoms as defined for substituted alkyl, or a lower alkyl group as defined above that has both from 1 to 5 substituents as defined above and is also interrupted by 1–5 atoms as defined above.

The term "alkylene" refers to a diradical of a branched or unbranched saturated hydrocarbon chain, preferably having from 1 to 20 carbon atoms, preferably 1–10 carbon atoms, more preferably 1–6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain, preferably having from 1 to 6 carbon atoms.

The term "substituted alkylene" refers to:
(1) an alkylene group as defined above having from 1 to 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
(2) an alkylene group as defined above that is interrupted by 1–5 atoms or groups independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or (3) an alkylene group as defined above that has both from 1 to 5 substituents as defined above and is also interrupted by 1–20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers(—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y-Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1–6, preferably 1, double bond (vinyl). Preferred alkenyl groups include ethenyl or vinyl (—CH=CH$_2$), 1-propylene or allyl (—CH$_2$CH=CH$_2$), isopropylene, (—C(CH$_3$)=CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heierocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1–6 sites of acetylene (triple bond) unsaturation. Preferred alkynyl groups include ethynyl, (—C≡CH), propargyl (or prop-1-yn-3-yl, —CH$_2$C≡CH), and the like. In the event that alkynyl is attached to nitrogen, the triple bond cannot be alpha to the nitrogen.

The term "substituted alkynyl" refers to an alkynyl group as defined above having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. Unless otherwise constrained by the definition, all substituents may optionally be further substituted by 1–3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by alkyl, carboxy, carboxyalkyl, aminocarbonyl, hydroxy, alkoxy, halogen, CF$_3$, amino, substituted amino, cyano, or —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO₂-alkyl, SO₂-aryl and —SO₂-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF₃, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH₂.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y-Z, in which Y is optionally substituted alkylene and Z is alkenyl, cycloalkenyl, or alkynyl, Unless otherwise constrained by the definition, all substituents may optionally be further substituted by 1–3 substituents chosen from alkyl, carboxy, carboxyalkyl, aminocarbonyl, hydroxy, alkoxy, halogen, CF₃, amino, substituted amino, cyano, and —S(O)$_n$R, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, CF₃, amino, substituted amino, cyano, or —S(O)$_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, bicyclo[2.2.1] heptane, 1,3,3-trimethylbicyclo[2.2.]hept-2-yl, (2,3,3-trimethylbicyclo[2.2.1]hept-2-yl), or cyclic alkyl groups to which is fused an aryl group, for example indane, and the like.

The term "substituted cycloalkyl" refers to cycloalkyl groups having from 1 to 5 substituents, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO₂-alkyl, SO₂-aryl and —SO₂-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF₃, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO₂-alkyl, SO₂-aryl and —SO₂-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF₃, amino, substituted amino, cyano, and —S(O)$_n$R, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazolyl, or benzothienyl). Examples of heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroaralkyl groups are exemplified by 3-pyridylmethyl, quinolin-8-ylethyl, 4-methoxythiazol-2-ylpropyl, and the like.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO₂-alkyl, SO₂-aryl and —SO₂-heteroaryl. Unless otherwise constrained by the definition, all substituents may optionally be further substituted by 1–3 substituents chosen from alkyl, carboxy, carboxyalkyl, aminocarbonyl, hydroxy, alkoxy, halogen, CF₃, amino, substituted amino, cyano, and —S(O)$_n$R, where R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group C(O)—. The term "thiocarbonyl" refers to a group —C(S)—. The term "carboxy" refers to a group C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed, and the pharmaceutically acceptable salts, pharmaceutically acceptable esters, prodrugs, hydrates and polymorphs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Nomenclature

The naming and numbering of the compounds of the invention is illustrated with a representative compound of Formula I in which $R^1$ is phenyl, $R^2$ is ethyl, $R^3$ is 3,5-dimethylfuran-2-yl, X is —NH—, and Y is methylene:

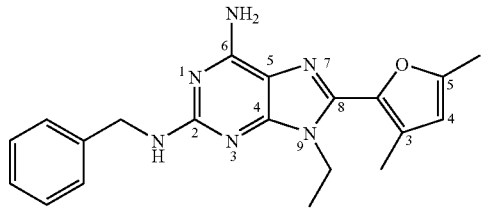

which is named:

2-benzylamino-8-(3,5-dimethylfuran-2-yl)-9-ethyl-9H-purin-6-ylamine.

The compounds of this invention can be prepared as outlined in the Reaction Schemes shown below.

REACTION SCHEME I

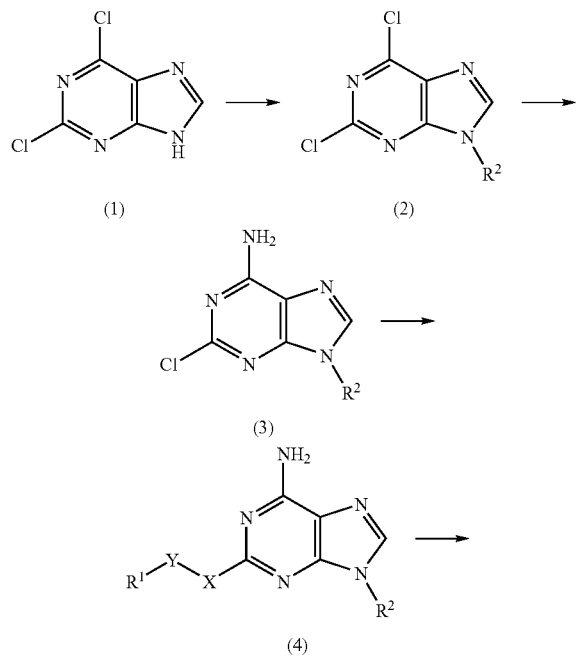

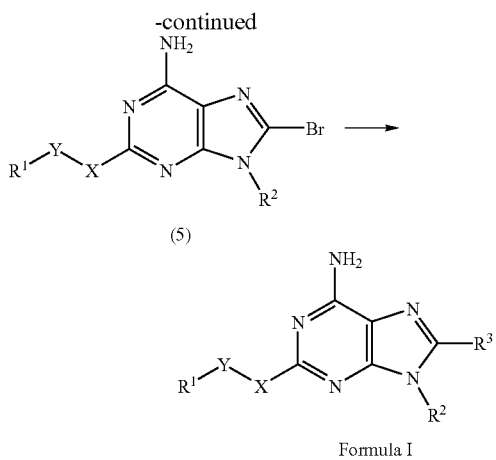

Formula I

Step 1—Preparation of Formula (2)

The compound of formula (2) is prepared conventionally from the commercially available compound of formula (1), 2,6-dichloropurine, by reaction with compound of the formula $R^2$Hal, where Hal is chloro, bromo, or iodo, preferably iodo. The reaction is carried out in the presence of a base, preferably potassium carbonate, in a polar solvent, preferably DMF. The reaction is carried out at a temperature of 10–40° C., preferably about room temperature, for about 6–32 hours, preferably about 16 hours. When the reaction is substantially complete, the product of formula (2) is isolated by conventional means, and the residue purified, for example by flash chromatography.

Step 2—Preparation of Formula (3)

The compound of formula (2) is then converted to a compound of formula (3) by reaction with liquid ammonia under pressure. The reaction is carried out at a temperature of 10–40° C., preferably about room temperature, for about 6–32 hours, preferably about 20 hours. When the reaction is substantially complete, the product of formula (3) is isolated by conventional means, for example by evaporation of the ammonia and purifying the residue, for example by flash chromatography.

Step 3—Preparation of Formula (4)

The compound of formula (3) is then converted to a compound of formula (4) in which X is —NH— by displacement of the 2-chloro moiety with excess amine of formula $R^1YNH_2$. The reaction is carried out under pressure, at a temperature of 100–150° C., preferably about 130° C., for about 6–32 hours, preferably about 24 hours. When the reaction is substantially complete, the product of formula (4) is isolated by conventional means, for example by removal of the amine under reduced pressure and purifying the residue, for example by chromatography on silica gel.

To prepare a compound of formula (4) in which X is oxygen or sulfur, the 2-chloro moiety is displaced from the compound of formula (3) by reaction with a compound of formula $R^1XM$, where X is oxygen or sulfur and M is an alkali metal. The reaction is carried out in an inert solvent, preferably DMF, at a temperature of about 50–120° C., for about 24–48 hours.

Step 4—Preparation of Formula (5)

The compound of formula (4) is then brominated to give a compound of formula (5) by reaction with N-bromosuccinimide, or a similar halogenating agent. The reaction is carried out in a polar solvent, preferably DMF, at a temperature of 0–40° C., preferably about room temperature, for about 10 minutes to 6 hours, preferably about 1 hour. When the reaction is substantially complete, the product of formula (5) is isolated by conventional means, for example by removal of the solvent under reduced pressure and purifying the residue, for example by chromatography on silica gel.

Step 5—Preparation of Formula I

The compound of formula (5) is then converted to a compound of Formula I by reaction with a compound of formula $R^3Sn\text{-}(tributyl)_3$, which are either commercially available or can be prepared by means well known to those skilled in the art, for example by reacting a compound of formula $R^3Hal$ with n-butyl lithium at −78° C. and reacting the anion thus formed with tributyltin chloride. The reaction is carried out in the presence of a palladium catalyst, preferably bis(triphenylphosphine)palladium dichloride, in an inert solvent, preferably tetrahydrofuran, at a temperature of 30° C. to the reflux temperature, preferably about 60° C., for about 1 to 10 hours, preferably about 3 hours. When the reaction is substantially complete, the product of Formula I is isolated by conventional means, for example by removal of the solvent under reduced pressure and purifying the residue, for example by chromatography on silica gel.

The methods used to prepare the compounds of this invention are not limited to those described above. Additional methods can be found in the following sources and are included by reference (J. March, Advanced Organic Chemistry; Reaction Mechanisms and Studies (1992), A Wiley Interscience Publications).

This invention also includes pro-drugs of the above-identified $A_{2A}$ antagonists. A pro-drug is a drug that has been chemically modified and may be biological inactive at its site of action, but which will be degraded or modified by one or more enzymatic or in vivo processes to the bioactive form. The pro-drugs of this invention should have a different pharmacokinetic profile to the parent enabling improved absorption across the mucosal epithelium, better salt formulation and/or solubility and improved systemic stability. The above-identified compounds may be preferably modified at one or more of the hydroxyl groups. The modifications may be (1) ester or carbamate derivatives which may be cleaved by esterases or lipases, for example; (2) peptides which may be recognized by specific or non-specific proteinase; or (3) derivatives that accumulate at a site of action through membrane selection or a pro-drug form or modified pro-drug form, or any combination of (1) to (3) above.

Utility, Testing and Administration

General Utility

The compounds of Formula I are effective in the treatment of conditions known to respond to administration of $A_{2A}$ adenosine receptor antagonists. Such conditions include, but are not limited to, movement disorders (Parkinson's disease, Huntington's Chorea, and catelepsy), and cerebral ischemia, excitotoxicity, cognitive and physiological disorders, depression, and the like.

Testing

Activity testing is conducted as described in those patents and patent applications referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. $17^{th}$ Ed. (1985) and "Modern Pharmaceutics", Marcel Dekker, Inc. $3^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and is generally administered in a pharmaceutically effective amount. Preferably, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50–200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (2)

A. Preparation of a Compound of Formula (2) where $R^2$ is Ethyl

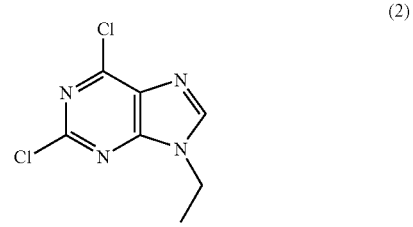

(2)

2,6-Dichloropurine (378 mg, 2.0 mmol) was dissolved in dimethylsulfoxide (10 mL), and dry potassium carbonate (345 mg, 2.5 mmol), and iodoethane (312 mg, 2.0 mmol) added. The mixture was stirred at room temperature for 16 hours, then the mixture was diluted with ice, acetic acid was added to adjust the pH to 5, and the solution was extracted with ethyl acetate. The combined extracts were washed with water, dried over sodium sulfate, filtered, and the filtrate evaporated in vacuo. The residue was purified by flash chromatography, eluting initially with cyclohexane-EtOAc (75:25) to give 2,6-dichloro-9-ethylpurine (280 mg, 65%), a compound of formula (2). mp 100–103° C.; UV $\lambda_{max}$ (MeOH) 214 nm ($\epsilon$ 22900), 274 ($\epsilon$ 9500), (pH 1) 213 nm ($\epsilon$ 22800), 273 ($\epsilon$ 9500), (pH 12) 214 nm ($\epsilon$ 17900), 260 ($\epsilon$ 7800), 266 ($\epsilon$ 8100); $^1$H NMR (Me$_2$SO-d$_6$) $\delta$ 1.45 (t, 3H, J=7.2 Hz, CH$_2$CH$_3$), 4.28 (q, 2H, J=7.2 Hz, CH$_2$CH$_3$), 8.77 (s, 1H, H-8). Anal. (C$_7$H$_6$Cl$_2$N$_4$) C, H, N.

After further elution with a gradient up to a final mixture of cyclohexane-EtOAc (50:50), the isomer 2,6-dichloro-7-ethylpurine (108 mg, 25%) was obtained. mp 173° C. (dec.)

B. Preparation of a Compound of Formula (2), Varying R$^2$

Similarly, following the procedure of 1A above, but replacing iodoethane by other alkyl halides or other compounds with suitable leaving groups, the following compounds of formula (3) are prepared:
2,6-dichloro-9-methylpurine;
2,6-dichloro-9-n-propylpurine;
2,6-dichloro-9-(isobutyl)purine;
2,6-dichloro-9-(2-fluoropropyl)purine;
2,6-dichloro-9-(n-pentyl)purine;
2,6-dichloro-9-(n-decyl)purine;
2,6-dichloro-9-allylpurine;
2,6-dichloro-9-(hept-4-enyl)purine;
2,6-dichloro-9-(prop-2-ynyl)purine;
2,6-dichloro-9-cyclohexylmethylpurine;
2,6-dichloro-9-phenylethylpurine;
2,6-dichloro-9-(4-methoxy)phenylethylpurine;
2,6-dichloro-9-(4-pyridylprop-1-yl)purine; and
2,6-dichloro-9-(4-piperidinbut-1-yl)purine.

EXAMPLE 2

Preparation of a Compound of Formula (3)

A. Preparation of a Compound of Formula (3) where R$^2$ is Ethyl

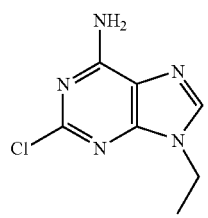

(3)

A solution of 2,6-dichloro-9-ethylpurine (2.7 g, 12.4 mmol), a compound of formula (2), in liquid ammonia (20 mL) was sealed in a stainless steel tube and set aside at room temperature for 20 hours. The solvent was removed in vacuo and the residue was purified by flash chromatography on a silica gel column eluting with EtOAc-cyclohexane (65:35) to give 2-chloro-9-ethyl-9H-purin-6-ylamine, a compound of formula (3) (2.28 g, 93%) as a chromatographically pure solid: mp 258–262° C.; $^1$H NMR (Me$_2$SO-d$_6$) $\delta$ 1.39 (t, 3H, J=7.3 Hz, CH$_2$CH$_3$), 4.13 (q, 2H, J=7.3 Hz, CH$_2$CH$_3$), 7.74 (s, 2H, NH$_2$), 8.18 (s, 1H, H-8). Anal. (C$_7$H$_7$ClN$_5$) C, H, N.

B. Preparation of a Compound of Formula (3), Varying R$^2$

Similarly, following the procedure of 2A above, but replacing 2,6-dichloro-9-ethylpurine by other compounds of formula (2), the following compounds of formula (3) are prepared:
2-chloro-9-methyl-9H-purin-6-ylamine;
2-chloro-9-n-propyl-9H-purin-6-ylamine;
2-chloro-9-(isobutyl)-9H-purin-6-ylamine;
2-chloro-9-(2-fluoropropyl)-9H-purin-6-ylamine;
2-chloro-9-(n-pentyl)-9H-purin-6-ylamine;
2-chloro-9-(n-decyl)-9H-purin-6-ylamine;
2-chloro-9-allyl-9H-purin-6-ylamine;
2-chloro-9-(hept-4-enyl)-9H-purin-6-ylamine;
2-chloro-9-(prop-2-ynyl)-9H-purin-6-ylamine;
2-chloro-9-cyclohexylmethyl-9H-purin-6-ylamine;
2-chloro-9-phenylethyl-9H-purin-6-ylamine;
2-chloro-9-(4-methoxy)phenylethyl-9H-purin-6-ylamine;
2-chloro-9-(4-pyridylprop-1-yl)-9H-purin-6-ylamine; and
2-chloro-9-(4-piperidinbut-1-yl)-9H-purin-6-ylamine.

EXAMPLE 3

Preparation of a Compound of Formula (4)

A. Preparation of a Compound of Formula (4) where R$^1$ is Phenyl, R$^2$ is Ethyl, X is —NH—, and Y is Methylene

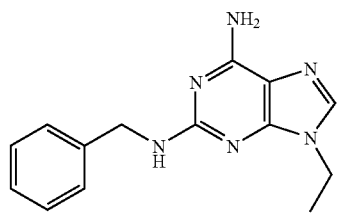

(4)

A mixture of 2-chloro-9-ethyl-9H-purin-6-ylamine (0.2 g, 1.01 mmol), a compound of formula (3), and 3 mL of benzylamine was heated in a steel bomb at 130° C. for 24 hours. The amine was removed from the reaction mixture by evaporation under reduced pressure, and the residue was chromatographed on a silica gel column, eluting with chloroform/methanol (95:5), to give pure 2-benzylamino-9-ethyl-9H-purin-6-ylamine, a compound of formula (4).

$^1$H NMR (Me$_2$SO-d$_6$) $\delta$ 1.31 (t, 3H, J=7.2 Hz, CH$_2$CH$_3$), 3.97 (q, 2H, J=7.2 Hz, CH$_2$CH$_3$) 4.48 (d, 2H, J=6.5 Hz, CH$_2$Ph),), 6.65 (s, 2H, NH$_2$), 6.79 (bs, 1H, NH), 7.14–7.37 (m, 5H, H-Ph), 7.71 (s, 1H, H-8). Anal. (C$_{14}$H$_{16}$N$_5$S) C, H, N.

B. Preparation of a Compound of Formula (4) where R$^2$ is Ethyl, X is —NH—, Varying R$^1$ and Y Similarly, following the procedure of 3A above, but replacing benzylamine by other amines of the formula R$^1$YNH$_2$, the following compounds of formula (4) were prepared:
2-(2-phenylethylamino)-9-ethyl-9H-purin-6-ylamine;

$^1$H NMR (Me$_2$SO-d$_6$) $\delta$ 1.37 (t, 3H, J=7.2 Hz, CH$_2$CH$_3$), 2.84 (q, 2H, J=7.3 Hz, CH$_2$CH$_2$Ph), 3.44 (m, 2H, NHCH$_2$CH$_2$), 4.01 (q, 2H, J=7.2 Hz, CH$_2$CH$_3$), 6.23 (t, 1H, J=7.3 Hz, NH), 6.62 (s, 2H, NH$_2$), 7.15–7.33 (m, 5H, H-Ph), 7.71 (s, 1H, H-8). Anal. (C$_{15}$H$_{18}$N$_6$) C, H, N.

2-(3-phenylpropylamino)-9-ethyl-9H-purin-6-ylamine;

$^1$H NMR (Me$_2$SO-d$_6$) δ 1.35 (t, 3H, J=7.2 Hz, CH$_2$CH$_3$), 1.83 (m, 2H, CH$_2$CH$_2$NH), 2.64 (t, 2H, J=7.2 Hz, CH$_2$CH$_2$Ph), 3.27 (m, 2H, CH$_2$CH$_2$NH), 3.99 (q, 2H, J=7.2 Hz, CH$_2$CH$_3$), 6.30 (t, 1H, J=5.6 Hz, NH), 6.59 (s, 2H, NH$_2$), 7.25 (m, 5H, H-Ph), 7.71 (s, 1H, H-8). Anal. (C$_{16}$H$_{20}$N$_6$) C, H, N.

2-(4-fluorophenyl)ethylamino-9-ethyl-9H-purin-6-ylamine;

$^1$H NMR (Me$_2$SO-d$_6$) δ 1.36 (t, 3H, J=7.2 Hz, CH$_2$CH$_3$), 2.83 (t, 2H, J=7.5 Hz, CH$_2$CH$_2$Ph),), 3.43 (q, 2H, J=7.8 Hz, CH$_2$CH$_2$Ph), 4.01 (q, 2H, J=7.2 Hz, CH$_2$CH$_3$), 6.30 (t, 1H, J=x Hz, NH), 6.66 (s, 2H, NH$_2$), 7.13 (m, 2H, H-Ph), 7.29 (m, 2H, H-Ph), 7.73 (s, 1H, H-8). Anal. (C$_{15}$H$_{17}$FN$_6$) C, H, N.

2-(4-chlorophenyl)ethylamino-9-ethyl-9H-purin-6-ylamine;

$^1$H NMR (Me$_2$SO-d$_6$) δ 1.37 (t, 3H, J=7.2 Hz, CH$_2$CH$_3$), 2.85 (t, 2H, J=7.7 Hz, CH$_2$CH$_2$Ph), 3.44 (q, 2H, J=7.7 Hz, CH$_2$CH$_2$Ph), 4.01 (q, 2H, J=7.3 Hz, CH$_2$CH$_3$), 6.23 (t, 1H, J=x Hz, NH), 6.67 (s, 2H, NH$_2$), 7.27–7.38 (m, 4H, H-Ph), 7.74 (s, 1H, H-8). Anal. (C$_{15}$H$_{17}$ClN$_6$) C, H, N;

2-(4-bromophenyl)ethylamino-9-ethyl-9H-purin-6-ylamine;

$^1$H NMR (Me$_2$SO-d$_6$) δ 1.37 (t, 3H, J=7.3 Hz, CH$_2$CH$_3$), 2.83 (t, 2H, J=7.7 Hz, CH$_2$CH$_2$Ph), 3.44 (q, 2H, J=7.4 Hz, CH$_2$CH$_2$Ph), 4.01 (q, 2H, J=7.3 Hz, CH$_2$CH$_3$), 6.32 (t, 1H, J=x Hz, NH), 6.67 (s, 2H, NH$_2$), 7.24 (d, 2H, J=8.3 Hz, H-Ph), 7.48 (d, 2H, J=8.3 Hz, H-Ph), 7.74 (s, 1H, H-8). Anal. (C$_{15}$H$_{17}$BrN$_6$) C, H, N;

2-(4-methylphenyl)ethylamino-9-ethyl-9H-purin-6-ylamine;

$^1$H NMR (Me$_2$SO-d$_6$) δ 1.37 (t, 3H, J=6.7 Hz, CH$_2$CH$_3$), 2.27 (s, 3H, CH$_3$), 2.80 (t, 2H, J=7.0 Hz, CH$_2$CH$_2$Ph), 3.42 (q, 2H, J=6.3 Hz, CH$_2$CH$_2$Ph), 4.02 (q, 2H, J=7.0 Hz, CH$_2$CH$_3$), 6.24 (t, 1H, J=x hz, NH), 6.66 (s, 2H, NH$_2$), 7.08–7.14 (m, 4H, H-Ph), 7.73 (s, 1H, H-8). Anal. (C$_{16}$H$_{20}$N$_6$) C, H, N;

2-(4-methoxyphenyl)ethylamino-9-ethyl-9H-purin-6-ylamine;

$^1$H NMR (Me$_2$SO-d$_6$) δ 1.38 (t, 3H, J=7.3 Hz, CH$_2$CH$_3$), 2.77 (t, 2H, J=7.8 Hz, CH$_2$CH$_2$Ph), 3.42 (q, 2H, J=7.8 Hz, CH$_2$CH$_2$Ph), 3.73 (s, □3H, OCH$_3$), 4.02 (q, 2H, J=7.3 Hz, CH$_2$CH$_3$), 6.22 (t, 1H, J=5.5 Hz, NH), 6.65 (s, 2H, NH$_2$), 6.87 (d, 2H, J=8.3 Hz, H-Ph), 7.19 (d, 2H, J=8.3 Hz, H-Ph), 7.73 (s, 1H, H-8). Anal. (C$_{16}$H$_{20}$N$_6$O) C, H, N; and 2-(3,4-dimethoxyphenyl)ethylamino-9-ethyl-9H-purin-6-ylamine;

$^1$H NMR (Me$_2$SO-d$_6$) δ 1.37 (t, 3H, J=7.2 Hz, CH$_2$CH$_3$), 2.78 (t, 2H, J=7.7 Hz, CH$_2$CH$_2$Ph), 3.45 (q, 2H, J=8.0 Hz, CH$_2$CH$_2$Ph), 3.72 (s, 3H, OCH$_3$), 3.74 (s, 3H, OCH$_3$), 4.02 (q, 2H, J=7.3 Hz, CH$_2$CH$_3$), 6.22 (t, 1H, J=x Hz, NH), 6.66 (s, 2H, NH$_2$), 6.76–6.89 (m, 3H, H-Ph), 7.73 (s, 1H, H-8). Anal. (C$_{17}$H$_{22}$N$_6$O$_2$) C, H, N.

C. Preparation of a Compound of Formula (4) where R$^1$ is Phenyl R$^2$ is Ethyl, X is —O—, and Y is Methylene

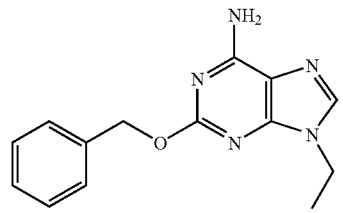

(4)

To a mixture of 2-chloro-9-ethyl-9H-purin-6-ylamine (0.2 g, 1.01 mmol), a compound of formula (3), and dry sodium hydroxide (5 mmol) was added benzyl alcohol (9.0 mmol). This mixture was heated at 85° C. for 3 hours. The solvent was then removed under reduced pressure and the residue was neutralized with 2N HCl and extracted with CHCl$_3$. The organic layer was dried (Na$_2$SO$_4$) and concentrated in vacuo. The residue was chromatographed on a silica gel column eluting with a mixture of ethyl acetate/cyclohexane/methanol (60/33/5) to give 2-benzyloxy-9-ethyl-9H-purin-6-ylamine as a chromatographically pure solid.

$^1$H NMR (Me$_2$SO-d$_6$) δ 1.38 (t, 3H, J=7.2 Hz, CH$_2$CH$_3$), 4.08 (q, 2H, J=7.2 Hz, CH$_2$CH$_3$) 5.32 (s, 2H, OCH$_2$Ph), 7.25 (s, 2H, NH$_2$), 7.34–7.50 (m, 5H, H-Ph), 7.98 (s, 1H, H-8). Anal. (C$_{14}$H$_{15}$N$_5$O) C, H, N.

D. Preparation of a Compound of Formula (4) where R$^2$ is Ethyl, X is —O—, varying R$^1$ and Y Similarly, following the procedure of 3C above, but replacing benzyl alcohol by other alcohols of the formula R$^1$YOH, the following compounds of formula (4) were prepared:

2-(2-phenylethoxy)-9-ethyl-9H-purin-6-ylamine;

$^1$H NMR (Me$_2$SO-d$_6$) δ 1.38 (t, 3H, J=7.2 Hz, CH$_2$CH$_3$), 3.02 (t, 2H, J=6.9 Hz, CH$_2$CH$_2$Ph), 4.08 (q, 2H, J=7.2 Hz, CH$_2$CH$_3$) 4.42 (t, 2H, J=7.0 Hz, OCH$_2$CH$_2$Ph), 7.21 (s, 2H, NH$_2$), 7.32 (br m, 5H, H-Ph), 7.96 (s, 1H, H-8). Anal. (C$_{15}$H$_{17}$N$_5$O) C, H, N.

2-(3-phenylpropoxy)-9-ethyl-9H-purin-6-ylamine;

$^1$H NMR (Me$_2$SO-d$_6$) δ 1.38 (t, 3H, J=7.2 Hz, CH$_2$CH$_3$), 2.00 (m, 2H, CH$_2$CH$_2$O), 2.74 (t, 2H, J=8.1 Hz, CH$_2$CH$_2$Ph), 4.07 (q, 2H, J=7.2 Hz, CH$_2$CH$_3$) 4.22 (t, 2H, J=6.4 Hz, CH$_2$CH$_2$O), 7.13–7.37 (m, 7H, H-Ph and NH$_2$), 7.96 (s, 1H, H-8). Anal. (C$_{16}$H$_{19}$N$_5$O) C, H, N.

2-[2-(4-methoxyphenyl)ethoxy]-9-ethyl-9H-purin-6-ylamine;

$^1$H NMR (Me$_2$SO-d$_6$) δ 1.38 (t, 3H, J=7.2 Hz, CH$_2$CH$_3$), 2.95 (t, 2H, J=6.0 Hz, CH$_2$CH$_2$Ph), 3.74 (s, 3H, OCH$_3$), 4.07 (q, 2H, J=7.2 Hz, CH$_2$CH$_3$), 4.36 (t, 2H, J=6.0 Hz, CH$_2$CH$_2$Ph), 6.89 (d, 2H, J=8.7 Hz, H-Ph), 7.18 (s, 2H, NH$_2$), 7.24 (d, 2H, J=6.0 Hz, Ph), 7.96 (s, 1H, H-8). Anal. (C$_{16}$H$_{19}$N$_5$O$_2$) C, H, N.

E. Preparation of a Compound of Formula (4) where R$^1$ is Phenyl, R$^2$ is Ethyl, X is —S—, and Y is Methylene

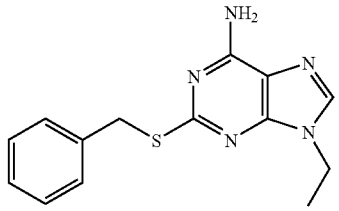

(4)

A mixture of 2-iodo-9-ethyl-9H-purin-6-ylamine (0.2 g, 0.69 mmol), 3 mL of benzyl mercaptan, and solid sodium hydroxide (200 mg, 5.0 mmol) was heated in a steel bomb at 100° C. for 24 hours. The reaction mixture was neutralized with 1N HCl and partitioned between water and chloroform. The organic layer was dried (Na2SO4), filtered and concentrated in vacuo, and the residue chromatographed on a silica gel column, eluting with a mixture of chloroform/methanol (97:3), to give 2-benzylthio-9-ethyl-9H-purin-6-ylamine, a compound of formula (4), as a chromatographically pure solid.

$^1$H NMR (Me$_2$SO-d$_6$) δ 1.39 (t, 3H, J=7.2 Hz, CH$_2$CH$_3$), 4.14 (q, 2H, J=7.2 Hz, CH$_2$CH$_3$) 4.36 (s, 2H, CH$_2$Ph), 7.19–7.44 (m, 7H, H-Ph and NH$_2$), 8.04 (s, 1H, H-8). Anal. (C$_{14}$H$_{15}$N$_5$S) C, H, N.

F. Preparation of a Compound of Formula (4) where $R^2$ is Ethyl, X is —S—, varying $R^1$ and Y Similarly, following the procedure of 3E above, but replacing benzyl mercaptan by other thiols of the formula $R^1YSH$, the following compound of formula (4) was prepared: 2-(2-phenylethylthio)-9-ethyl-9H-purin-6-ylamine $^1H$ NMR (Me$_2$SO-d$_6$) δ 1.42 (t, 3H, J=7.1 Hz, CH$_2$CH$_3$), 2.99 (m, 2H, CH$_2$CH$_2$Ph), 3.29 (m, 2H, SCH$_2$CH$_2$Ph), 4.16 (q, 2H, J=7.3 Hz, CH$_2$CH$_3$), 7.19–7.44 (m, 7H, H-Ph and NH$_2$), 8.05 (s, 1H, H-8). Anal. (C$_{15}$H$_{17}$N$_5$S) C, H, N.

G. Preparation of a Compound of Formula (4), Varying $R^1$, $R^2$, X, and Y

Similarly, following the procedure of 3A, 3C, and 3E above, but optionally replacing 2-chloro-9-ethyl-9H-purin-6-ylamine by other compounds of formula (3), optionally replacing benzylamine by other amines of the formula $R^1YNH_2$, optionally replacing benzyl alcohol by other alcohols of the formula $R^1YOH$, or optionally replacing benzyl mercaptan by other thiols of the formula $R^1YSH$, the following compounds of formula (4) are prepared:

2-(2-phenylethylamino)-9-methyl-9H-purin-6-ylamine;
2-(3-phenylpropylamino)-9-methyl-9H-purin-6-ylamine;
2-(2-phenylethoxy)-9-methyl-9H-purin-6-ylamine;
2-(3-phenylpropoxy)-9-methyl-9H-purin-6-ylamine;
2-(2-phenylethylthio)-9-methyl-9H-purin-6-ylamine;
2-(3-phenylpropylthio)-9-methyl-9H-purin-6-ylamine;
2-(2-phenylethylamino)-9-n-propyl-9H-purin-6-ylamine;
2-(3-phenylpropylamino)-9-n-propyl-9H-purin-6-ylamine;
2-(2-phenylethoxy)-9-n-propyl-9H-purin-6-ylamine;
2-(3-phenylpropoxy)-9-n-propyl-9H-purin-6-ylamine;
2-(2-phenylethylthio)-9-n-propyl-9H-purin-6-ylamine;
2-(3-phenylpropylthio)-9-n-propyl-9H-purin-6-ylamine;
2-(2-phenylethylamino)-9-isobutyl-9H-purin-6-ylamine;
2-(3-phenylpropylamino)-9-isobutyl-9H-purin-6-ylamine;
2-(2-phenylethoxy)-9-isobutyl-9H-purin-6-ylamine;
2-(3-phenylpropoxy)-9-isobutyl-9H-purin-6-ylamine;
2-(2-phenylethylthio)-9-isobutyl-9H-purin-6-ylamine;
2-(3-phenylpropylthio)-9-isobutyl-9H-purin-6-ylamine;
2-(2-phenylethylamino)-9-(2-fluoropropyl)-9H-purin-6-ylamine;
2-(3-phenylpropylamino)-9-(2-fluoropropyl)-9H-purin-6-ylamine;
2-(2-phenylethoxy)-9-(2-fluoropropyl)-9H-purin-6-ylamine;
2-(3-phenylpropoxy)-9-(2-fluoropropyl)-9H-purin-6-ylamine;
2-(2-phenylethylthio)-9-(2-fluoropropyl)-9H-purin-6-ylamine;
2-(3-phenylpropylthio)-9-(2-fluoropropyl)-9H-purin-6-ylamine;
2-(2-phenylethylamino)-9-(n-pentyl)-9H-purin-6-ylamine;
2-(3-phenylpropylamino)-9-(n-pentyl)-9H-purin-6-ylamine;
2-(2-phenylethoxy)-9-(n-pentyl)-9H-purin-6-ylamine;
2-(3-phenylpropoxy)-9-(n-pentyl)-9H-purin-6-ylamine;
2-(2-pbenylethylthio)-9-(n-pentyl)-9H-purin-6-ylamine;
2-(3-phenylpropylthio)-9-(n-pentyl)-9H-purin-6-ylamine;
2-(2-phenylethylamino)-9-(n-decyl)-9H-purin-6-ylamine;
2-(3-phenylpropylamino)-9-(n-decyl)-9H-purin-6-ylamine;
2-(2-phenylethoxy)-9-(n-decyl)-9H-purin-6-ylamine;
2-(3-phenylpropoxy)-9-(n-decyl)-9H-purin-6-ylamine;
2-(2-phenylethylthio)-9-(n-decyl)-9H-purin-6-ylamine;
2-(3-phenylpropylthio)-9-(n-decyl)-9H-purin-6-ylamine;
2-(2-phenylethylamino)-9-allyl-9H-purin-6-ylamine;
2-(3-phenylpropylamino)-9-allyl-9H-purin-6-ylamine;
2-(2-phenylethoxy)-9-allyl-9H-purin-6-ylamine;
2-(3-phenylpropoxy)-9-allyl-9H-purin-6-ylamine;
2-(2-phenylethylthio)-9-allyl-9H-purin-6-ylamine;
2-(3-phenylpropylthio)-9-allyl-9H-purin-6-ylamine;
2-(2-phenylethylamino)-9-(hept-4-enyl)-9H-purin-6-ylamine;
2-(3-phenylpropylamino)-9-(hept-4-enyl)-9H-purin-6-ylamine;
2-(2-phenylethoxy)-9-(hept-4-enyl)-9H-purin-6-ylamine;
2-(3-phenylpropoxy)-9-(hept-4-enyl)-9H-purin-6-ylamine;
2-(2-phenylethylthio)-9-(hept-4-enyl)-9H-purin-6-ylamine;
2-(3-phenylpropylthio)-9-(hept-4-enyl)-9H-purin-6-ylamine;
2-(2-phenylethylamino)-9-(prop-2-ynyl)-9H-purin-6-ylamine;
2-(3-phenylpropylamino)-9-(prop-2-ynyl)-9H-purin-6-ylamine;
2-(2-phenylethoxy)-9-(prop-2-ynyl)-9H-purin-6-ylamine;
2-(3-phenylpropoxy)-9-(prop-2-ynyl)-9H-purin-6-ylamine;
2-(2-phenylethylthio)-9-(prop-2-ynyl)-9H-purin-6-ylamine;
2-(3-phenylpropylthio)-9-(prop-2-ynyl)-9H-purin-6-ylamine;
2-(2-phenylethylamino)-9-cyclohexylmethyl-9H-purin-6-ylamine;
2-(3-phenylpropylamino)-9-cyclohexylmethyl-9H-purin-6-ylamine;
2-(2-phenylethoxy)-9-cyclohexylmethyl-9H-purin-6-ylamine;
2-(3-phenylpropoxy)-9-cyclohexylmethyl-9H-purin-6-ylamine;
2-(2-phenylethylthio)-9-cyclohexylmethyl-9H-purin-6-ylamine;
2-(3-phenylpropylthio)-9-cyclohexylmethyl-9H-purin-6-ylamine;
2-(2-phenylethylamino)-9-phenylethyl-9H-purin-6-ylamine;
2-(3-phenylpropylamino)-9-phenylethyl-9H-purin-6-ylamine;
2-(2-phenylethoxy)-9-phenylethyl-9H-purin-6-ylamine;
2-(3-phenylpropoxy)-9-phenylethyl-9H-purin-6-ylamine;
2-(2-phenylethylthio)-9-phenylethyl-9H-purin-6-ylamine;
2-(3-phenylpropylthio)-9-phenylethyl-9H-purin-6-ylamine;
2-(2-phenylethylamino)-9-(4-methoxyphenyl)ethyl-9H-purin-6-ylamine;
2-(3-phenylpropylamino)-9-(4-methoxyphenyl)ethyl-9H-purin-6-ylamine;
2-(2-phenylethoxy)-9-(4-methoxyphenyl)ethyl-9H-purin-6-ylamine;
2-(3-phenylpropoxy)-9-(4-methoxyphenyl)ethyl-9H-purin-6-ylamine;
2-(2-phenylethylthio)-9-(4-methoxyphenyl)ethyl-9H-purin-6-ylamine;
2-(3-phenylpropylthio)-9-(4-methoxyphenyl)ethyl-9H-purin-6-ylamine;
2-(2-phenylethylamino)-9-(4-pyridylprop-1-yl)-9H-purin-6-ylamine;
2-(3-phenylpropylamino)-9-(4-pyridylprop-1-yl)-9H-purin-6-ylamine;
2-(2-phenylethoxy)-9-(4-pyridylprop-1-yl)-9H-purin-6-ylamine;
2-(3-phenylpropoxy)-9-(4-pyridylprop-1-yl)-9H-purin-6-ylamine;
2-(2-phenylethylthio)-9-(4-pyridylprop-1-yl)-9H-purin-6-ylamine;
2-(3-phenylpropylthio)-9-(4-pyridylprop-1-yl)-9H-purin-6-ylamine;
2-(2-phenylethylamino)-9-(4-piperidinbut-1-yl)-9H-purin-6-ylamine;

2-(3-phenylpropylamino)-9-(4-piperidinbut-1-yl)-9H-purin-6-ylamine;
2-(2-phenylethoxy)-9-(4-piperidinbut-1-yl)-9H-purin-6-ylamine;
2-(3-phenylpropoxy)-9-(4-piperidinbut-1-yl)-9H-purin-6-ylamine;
2-(2-phenylethylthio)-9-(4-piperidinbut-1-yl)-9H-purin-6-ylamine; and
2-(3-phenylpropylthio)-9-(4-piperidinbut-1-yl)-9H-purin-6-ylamine.

EXAMPLE 4

Preparation of a Compound of Formula (5)

A. Preparation of a Compound of Formula (5) where $R^1$ is Phenyl, $R^2$ is Ethyl, X is —NH—, and Y is Methylene

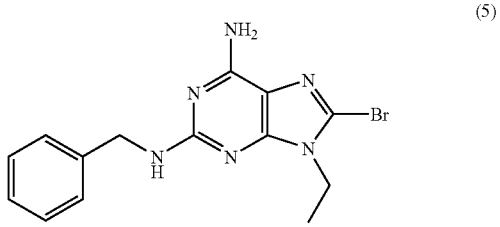

(5)

To a solution of 2-benzylamino-9-ethyl-9H-purin-6-ylamine (1.0 mmol), a compound of formula (4), in 10 mL of dry DMF was added N-bromosuccinimide (267 mg, 1.5 mmol). The reaction mixture was stirred at room temperature for 1 hour. The solvent was then removed in vacuo and the residue partitioned between water and chloroform. The organic layer was washed with 1N sodium hydroxide, dried ($Na_2SO_4$), filtered, and the filtrate concentrated in vacuo. The residue was chromatographed on a silica gel column, eluting with chloroform/methanol; (98/2), to give 2-benzylamino-8-bromo-9-ethyl-9H-purin-6-ylamine as a chromatographically pure solid.

$^1$H NMR ($Me_2SO-d_6$) δ 1.25 (t, 3H, J=7.2 Hz, $CH_2CH_3$), 3.99 (q, 2H, J=7.3 Hz, $CH_2CH_3$), 4.47 (d, 2H, J=6.5 Hz, $CH_2Ph$), 6.85 (s, 2H, $NH_2$), 6.99 (bs, 1H, NH), 7.14–7.40 (m, 5H, H-Ph). Anal. ($C_{14}H_{15}BrN_6$) C, H, N.

B. Preparation of a Compound of Formula (5) where $R^2$ is Ethyl, X is —NH—, Varying $R^1$ and Y Similarly, following the procedure of 4A above, but replacing 2-benzylamino-9-ethyl-9H-purin-6-ylamine by other compounds of formula (4), the following compounds of formula (5) were prepared:

2-(2-phenylethylamino)-8-bromo-9-ethyl-9H-purin-6-ylamine;
$^1$H NMR ($Me_2SO-d_6$) δ 1.30 (t, 3H, J=7.2 Hz, $CH_2CH_3$), 2.84 (t, 2H, J=8.1 Hz, $CH_2CH_2Ph$),), 3.45 (q, 2H, J=8.3 Hz, $CH_2CH_2Ph$), 4.02 (q, 2H, J=7.0 Hz, $CH_2CH_3$), 6.45 (bs, 1H, NH), 6.85 (s, 2H, $NH_2$), 7.28 (m, 5H, H-Ph). Anal. ($C_{15}H_{17}BrN_6$) C, H, N.

2-(3-phenylpropylamino)-8-bromo-9-ethyl-9H-purin-6-ylamine;
$^1$H NMR ($Me_2SO-d_6$) δ 1.28 (t, 3H, J=7.2 Hz, $CH_2CH_3$), 1.83 (m, 2H, $CH_2CH_2NH$), 2.64 (t, 2H, J=7.2 Hz, $CH_2CH_2Ph$), 3.27 (m, 2H, $CH_2CH_2NH$), 4.00 (q, 2H, J=7.2 Hz, $CH_2CH_3$), 6.49 (t, 1H, J=4.0 Hz, NH), 6.80 (s, 2H, $NH_2$), 7.24 (m, 5H, H-Ph). Anal. ($C_{16}H_{19}BrN_6$) C, H, N.

2-(4-fluorophenylethylamino)-8-bromo-9-ethyl-9H-purin-6-ylamine;
$^1$H NMR ($Me_2SO-d_6$) δ 1.29 (t, 3H, J=7.0 Hz, $CH_2CH_3$), 2.83 (t, 2H, J=7.4 Hz, CH2CH2Ph), ), 3.43 (q, 2H, J=6.6 Hz, CH2CH2Ph), 4.02 (q, 2H, J=7.0 Hz, CH2CH3), 6.50 (bs, 1H, NH), 6.87 (s, 2H, NH2), 7.11 (m, 2H, H-Ph), 7.30 (m, 2H, H-Ph). Anal. (C15H16BrFN6) C, H, N.

2-(4-chlorophenylethylamino)-8-bromo-9-ethyl-9H-purin-6-ylamine;
$^1$H NMR ($Me_2SO-d_6$) δ 1.29 (t, 3H, J=7.0 Hz, $CH_2CH_3$), 2.84 (t, 2H, J=7.2 Hz, $CH_2CH_2Ph$), 3.44 (q, 2H, J=7.0 Hz, $CH_2CH_2Ph$), 4.01 (q, 2H, J=7.0 Hz, $CH_2CH_3$), 6.50 (bs, 1H, NH), 6.86 (s, 2H, $NH_2$), 7.26–7.38 (m, 4H, H-Ph). Anal. ($C_{15}H_{16}BrClN_6$) C, H, N.

2-(4-bromophenylethylamino)-8-bromo-9-ethyl-9H-purin-6-ylamine;
$^1$H NMR ($Me_2SO-d_6$) δ 1.29 (t, 3H, J=7.0 Hz, $CH_2CH_3$), 2.82 (t, 2H, J=7.7 Hz, $CH_2CH_2Ph$), 3.42 (q, 2H, J=7.4 Hz, $CH_2CH_2Ph$), 4.01 (q, 2H, J=7.2 Hz, $CH_2CH_3$), 6.52 (bs, 1H, NH), 6.87 (s, 2H, $NH_2$), 7.23 (d, 2H, J=8.1 Hz, HPh), 7.48 (d, 2H, J=8.1 Hz, H-Ph), 7.74 (s, 1H, H-8). Anal. ($C_{15}H_{16}Br_2N_6$) C, H, N.

2-(4-methylphenylethylamino)-8-bromo-9-ethyl-9H-purin-6-ylamine;
$^1$H NMR ($Me_2SO-d_6$) δ 1.30 (t, 3H, J=7.0 Hz, $CH_2CH_3$), 2.28 (s, 3H, $CH_3$), 2.79 (t, 2H, J=7.7 Hz, $CH_2CH_2Ph$), 3.42 (q, 2H, J=7.7 Hz, $CH_2CH_2Ph$), 4.02 (q, 2H, J=7.2 Hz, $CH_2CH_3$), 6.45 (bs, 1H, NH), 6.86 (s, 2H, $NH_2$), 7.09–7.18 (m, 4H, H-Ph). Anal. ($C_{16}H_{20}BrN_6$) C, H, N.

2-(4-methoxyphenylethylamino)-8-bromo-9-ethyl-9H-purin-6-ylamine;
$^1$H NMR ($Me_2SO-d_6$) δ 1.30 (t, 3H, J=7.1 Hz, $CH_2CH_3$), 2.77 (t, 2H, J=8.1 Hz, $CH_2CH_2Ph$), 3.41 (q, 2H, J=8.4 Hz, $CH_2CH_2Ph$), 3.73 (s, 3H, $OCH_3$), 4.02 (q, 2H, J=7.3 Hz, $CH_2CH_3$), 6.42 (bs, 1H, NH), 6.86 (m, 4H, H-Ph and $NH_2$), 7.18 (d, 2H, J=8.6 Hz, H-Ph). Anal. ($C_{16}H_{19}BrN_6O$) C, H, N.

2-(3,4-dimethoxyphenylethylamino)-8-bromo-9-ethyl-9H-purin-6-ylamine;
$^1$H NMR ($Me_2SO-d_6$) δ 1.29 (t, 3H, J=7.0 Hz, $CH_2CH_3$), 2.76 (t, 2H, J=8.1 Hz, $CH_2CH_2Ph$), 3.43 (q, 2H, J=8.1 Hz, $CH_2CH_2Ph$), 3.72 (s, 3H, $OCH_3$), 3.74 (s, 3H, $OCH_3$), 4.01 (q, 2H, J=7.0 Hz, $CH_2CH_3$), 6.43 (bs, 1H, NH), 6.73–6.89 (m, 5H, H-Ph and $NH_2$). Anal. ($C_{17}H_{21}BrN_6O_2$) C, H, N.

2-(4-hydroxyphenylethylamino)-8-bromo-9-ethyl-9H-purin-6-ylamine;
$^1$H NMR ($Me_2SO-d_6$) δ 1.29 (t, 3H, J=7.0 Hz, $CH_2CH_3$), 2.71 (t, 2H, J=8.1 Hz, $CH_2CH_2Ph$), 3.37 (m, 2H, $CH_2CH_2Ph$), 4.01 (q, 2H, J=7.0 Hz, $CH_2CH_3$), 6.40 (t, 1H, J=?, NH), 6.69 (d, 2H, J=8.4 Hz, H-Ph), 6.83 (s, 2H, $NH_2$), 7.05 (d, 2H, J=8.4 Hz, H-Ph), 9.16 (s, 1H, OH), Anal. ($C_{15}H_{17}BrN_6O$) C, H, N.

2-(3,4-dihydroxyphenylethylamino)-8-bromo-9-ethyl-9H-purin-6-ylamine;
$^1$H NMR ($Me_2SO-d_6$) δ 1.30 (t, 3H, J=7.0 Hz, $CH_2CH_3$), 2.65 (t, 2H, J=8.1 Hz, $CH_2CH_2Ph$), 3.36 (m, 2H, $CH_2CH_2Ph$), 4.02 (q, 2H, J=7.0 Hz, $CH_2CH_3$), 6.3 (t, 1H, J=x Hz, NH), 6.48–6.68 (m, 3H, H-Ph), 6.85 (s, 2H, $NH_2$), 8.66 (s, 1H, OH), 8.76 (s, 1H, OH). Anal. ($C_{15}H_{17}BrN_6O_2$) C, H, N.

2-(2-phenylethoxy)-8-bromo-9-ethyl-9H-purin-6-ylamine;
$^1$H NMR ($Me_2SO-d_6$) δ 1.31 (t, 3H, J=7.1 Hz, $CH_2CH_3$), 3.02 (t, 2H, J=6.9 Hz, $CH_2CH_2Ph$), 4.07 (q, 2H, J=7.2 Hz, $CH_2CH_3$) 4.42 (t, 2H, J=7.0 Hz, $OCH_2CH_2Ph$), 7.20–7.34 (m, 4H, H-Ph), 7.41 (s, 2H, $NH_2$). Anal. ($C_{15}H_{16}BrN_5O$) C, H, N.

2-benzyloxy-8-bromo-9-ethyl-9H-purin-6-ylamine;

$^1$H NMR (Me$_2$SO-d$_6$) δ 1.30 (t, 3H, J=7.0 Hz, CH$_2$CH$_3$), 4.08 (q, 2H, J=7.0 Hz, CH$_2$CH$_3$) 5.32 (s, 2H, OCH$_2$Ph), 7.30–750 (m, 7H, H-Ph and NH$_2$). Anal. (C$_{14}$H$_{14}$BrN$_5$O) C, H, N.

2-(3-phenylpropoxy)-8-bromo-9-ethyl-9H-purin-6-ylamine;
$^1$H NMR (Me$_2$SO-d$_6$) δ 1.30 (t, 3H, J=7.2 Hz, CH$_2$CH$_3$), 2.00 (m, 2H, CH$_2$CH$_2$O), 2.73 (t, 2H, J=7.0 Hz, CH$_2$CH$_2$Ph), 4.06 (q, 2H, J=7.2 Hz, CH$_2$CH$_3$) 4.22 (t, 2H, J=6.5 Hz, CH$_2$CH$_2$O), 7.15–7.35 (m, 5H, H-Ph), 7.38 (s, 2H, NH$_2$). Anal. (C$_{16}$H$_{18}$BrN$_5$O) C, H, N.

2-[2-(4-methoxyphenyl)propoxy]-8-bromo-9-ethyl-9H-purin-6-ylamine;
$^1$H NMR (Me$_2$SO-d$_6$) δ 1.31 (t, 3H, J=7.1 Hz, CH$_2$CH$_3$), 2.95 (t, 2H, J=6.9 Hz, CH$_2$CH$_2$Ph), 3.74 (s, 3H, OCH$_3$), 4.07 (q, 2H, J=7.1 Hz, CH$_2$CH$_3$), 4.37 (t, 2H, J=6.9 Hz, CH$_2$CH$_2$Ph), 6.89 (d, 2H, J=8.7 Hz, H-Ph) 7.24 (d, 2H, J=8.7 Hz, H-Ph), 7.40 (s, 2H, NH$_2$). Anal. (C$_{16}$H$_{18}$BrN$_5$O$_2$) C, H, N.

2-benzylthio-8-bromo-9-ethyl-9H-purin-6-ylamine;
$^1$H NMR (Me$_2$SO-d$_6$) δ 1.31 (t, 3H, J=7.2 Hz, CH$_2$CH$_3$), 4.14 (q, 2H, J=6.9 Hz, CH$_2$CH$_3$) 4.36 (s, 2H, CH$_2$Ph), 7.26–7.59 (m, 7H, H-Ph and NH$_2$). Anal. (C$_{14}$H$_{14}$BrN$_5$S) C, H, N. and 2-(2-phenylethylthio)-8-bromo-9-ethyl-9H-purin-6-ylamine;
$^1$H NMR (Me$_2$SO-d$_6$) δ 1.34 (t, 3H, J=7.0 Hz, CH$_2$CH$_3$), 2.98 (m, 2H, CH$_2$CH$_2$Ph), 3.28 (m, 2H, SCH$_2$CH$_2$Ph), 4.14 (q, 2H, J=7.3 Hz, CH$_2$CH$_3$), 7.22 (m, 1H, H-Ph), 7.32 (m, 4H, H-Ph and NH$_2$), 7.47 (m, 2H, H-Ph). Anal. (C$_{15}$H$_{16}$BrN$_5$S) C, H, N.

C. Preparation of a Compound of Formula (5), varying R$^1$, R$^2$, X, and Y

Similarly, following the procedure of 4A above, but optionally replacing 2-benzylamino-9-ethyl-9H-purin-6-ylamine by other compounds of formula (4), the following compounds of formula (5) are prepared:

2-(2-phenylethylamino)-8-bromo-9-methyl-9H-purin-6-ylamine;
2-(3-phenylpropylamino)-8-bromo-9-methyl-9H-purin-6-ylamine;
2-(2-phenylethoxy)-8-bromo-9-methyl-9H-purin-6-ylamine;
2-(3-phenylpropoxy)-8-bromo-9-methyl-9H-purin-6-ylamine;
2-(2-phenylethylthio)-8-bromo-9-methyl-9H-purin-6-ylamine;
2-(3-phenylpropylthio)-8-bromo-9-methyl-9H-purin-6-ylamine;
2-(2-phenylethylamino)-8-bromo-9-n-propyl-9H-purin-6-ylamine;
2-(3-phenylpropylamino)-8-bromo-9-n-propyl-9H-purin-6-ylamine;
2-(2-phenylethoxy)-8-bromo-9-n-propyl-9H-purin-6-ylamine;
2-(3-phenylpropoxy)-8-bromo-9-n-propyl-9H-purin-6-ylamine;
2-(2-phenylethylthio)-8-bromo-9-n-propyl-9H-purin-6-ylamine;
2-(3-phenylpropylthio)-8-bromo-9-n-propyl-9H-purin-6-ylamine;
2-(2-phenylethylamino)-8-bromo-9-isobutyl-9H-purin-6-ylamine;
2-(3-phenylpropylamino)-8-bromo-9-isobutyl-9H-purin-6-ylamine;
2-(2-phenylethoxy)-8-bromo-9-isobutyl-9H-purin-6-ylamine;
2-(3-phenylpropoxy)-8-bromo-9-isobutyl-9H-purin-6-ylamine;
2-(2-phenylethylthio)-8-bromo-9-isobutyl-9H-purin-6-ylamine;
2-(3-phenylpropylthio)-8-bromo-9-isobutyl-9H-purin-6-ylamine;
2-(2-phenylethylamino)-8-bromo-9-(2-fluoropropyl)-9H-purin-6-ylamine;
2-(3-phenylpropylamino)-8-bromo-9-(2-fluoropropyl)-9H-purin-6-ylamine;
2-(2-phenylethoxy)-8-bromo-9-(2-fluoropropyl)-9H-purin-6-ylamine;
2-(3-phenylpropoxy)-8-bromo-9-(2-fluoropropyl)-9H-purin-6-ylamine;
2-(2-phenylethylthio)-8-bromo-9-(2-fluoropropyl)-9H-purin-6-ylamine;
2-(3-phenylpropylthio)-8-bromo-9-(2-fluoropropyl)-9H-purin-6-ylamine;
2-(2-phenylethylamino)-8-bromo-9-(n-pentyl)-9H-purin-6-ylamine;
2-(3-phenylpropylamino)-8-bromo-9-(n-pentyl)-9H-purin-6-ylamine;
2-(2-phenylethoxy)-8-bromo-9-(n-pentyl)-9H-purin-6-ylamine;
2-(3-phenylpropoxy)-8-bromo-9-(n-pentyl)-9H-purin-6-ylamine;
2-(2-phenylethylthio)-8-bromo-9-(n-pentyl)-9H-purin-6-ylamine;
2-(3-phenylpropylthio)-8-bromo-9-(n-pentyl)-9H-purin-6-ylamine;
2-(2-phenylethylamino)-8-bromo-9-(n-decyl)-9H-purin-6-ylamine;
2-(3-phenylpropylamino)-8-bromo-9-(n-decyl)-9H-purin-6-ylamine;
2-(2-phenylethoxy)-8-bromo-9-(n-decyl)-9H-purin-6-ylamine;
2-(3-phenylpropoxy)-8-bromo-9-(n-decyl)-9H-purin-6-ylamine;
2-(2-phenylethylthio)-8-bromo-9-(n-decyl)-9H-purin-6-ylamine;
2-(3-phenylpropylthio)-8-bromo-9-(n-decyl)-9H-purin-6-ylamine;
2-(2-phenylethylamino)-8-bromo-9-allyl-9H-purin-6-ylamine;
2-(3-phenylpropylamino)-8-bromo-9-allyl-9H-purin-6-ylamine;
2-(2-phenylethoxy)-8-bromo-9-allyl-9H-purin-6-ylamine;
2-(3-phenylpropoxy)-8-bromo-9-allyl-9H-purin-6-ylamine;
2-(2-phenylethylthio)-8-bromo-9-allyl-9H-purin-6-ylamine;
2-(3-phenylpropylthio)-8-bromo-9-allyl-9H-purin-6-ylamine;
2-(2-phenylethylamino)-8-bromo-9-(hept-4-enyl)-9H-purin-6-ylamine;
2-(3-phenylpropylamino)-8-bromo-9-(hept-4-enyl)-9H-purin-6-ylamine;
2-(2-phenylethoxy)-8-bromo-9-(hept-4-enyl)-9H-purin-6-ylamine;
2-(3-phenylpropoxy)-8-bromo-9-(hept-4-enyl)-9H-purin-6-ylamine;
2-(2-phenylethylthio)-8-bromo-9-(hept-4-enyl)-9H-purin-6-ylamine;
2-(3-phenylpropylthio)-8-bromo-9-(hept-4-enyl)-9H-purin-6-ylamine;
2-(2-phenylethylamino)-8-bromo-9-(prop-2-ynyl)-9H-purin-6-ylamine;
2-(3-phenylpropylamino)-8-bromo-9-(prop-2-ynyl)-9H-purin-6-ylamine;

2-(2-phenylethoxy)-8-bromo-9-(prop-2-ynyl)-9H-purin-6-ylamine;
2-(3-phenylpropoxy)-8-bromo-9-(prop-2-ynyl)-9H-purin-6-ylamine;
2-(2-phenylethylthio)-8-bromo-9-(prop-2-ynyl)-9H-purin-6-ylamine;
2-(3-phenylpropylthio)-8-bromo-9-(prop-2-ynyl)-9H-purin-6-ylamine;
2-(2-phenylethylamino)-8-bromo-9-cyclohexylmethyl-9H-purin-6-ylamine;
2-(3-phenylpropylamino)-8-bromo-9-cyclohexylmethyl-9H-purin-6-ylamine;
2-(2-phenylethoxy)-8-bromo-9-cyclohexylmethyl-9H-purin-6-ylamine;
2-(3-phenylpropoxy)-8-bromo-9-cyclohexylmethyl-9H-purin-6-ylamine;
2-(2-phenylethylthio)-8-bromo-9-cyclohexylmethyl-9H-purin-6-ylamine;
2-(3-phenylpropylthio)-8-bromo-9-cyclohexylmethyl-9H-purin-6-ylamine;
2-(2-phenylethylamino)-8-bromo-9-phenylethyl-9H-purin-6-ylamine;
2-(3-phenylpropylamino)-8-bromo-9-phenylethyl-9H-purin-6-ylamine;
2-(2-phenylethoxy)-8-bromo-9-phenylethyl-9H-purin-6-ylamine;
2-(3-phenylpropoxy)-8-bromo-9-phenylethyl-9H-purin-6-ylamine;
2-(2-phenylethylthio)-8-bromo-9-phenylethyl-9H-purin-6-ylamine;
2-(3-phenylpropylthio)-8-bromo-9-phenylethyl-9H-purin-6-ylamine;
2-(2-phenylethylamino)-8-bromo-9-(4-methoxyphenyl)ethyl-9H-purin-6-ylamine;
2-(3-phenylpropylamino)-8-bromo-9-(4-methoxyphenyl)ethyl-9H-purin-6-ylamine;
2-(2-phenylethoxy)-8-bromo-9-(4-methoxyphenyl)ethyl-9H-purin-6-ylamine;
2-(3-phenylpropoxy)-8-bromo-9-(4-methoxyphenyl)ethyl-9H-purin-6-ylamine;
2-(2-phenylethylthio)-8-bromo-9-(4-methoxyphenyl)ethyl-9H-purin-6-ylamine;
2-(3-phenylpropylthio)-8-bromo-9-(4-methoxyphenyl)ethyl-9H-purin-6-ylamine;
2-(2-phenylethylamino)-8-bromo-9-(4-pyridylprop-1-yl)-9H-purin-6-ylamine;
2-(3-phenylpropylamino)-8-bromo-9-(4-pyridylprop-1-yl)-9H-purin-6-ylamine;
2-(2-phenylethoxy)-8-bromo-9-(4-pyridylprop-1-yl)-9H-purin-6-ylamine;
2-(3-phenylpropoxy)-8-bromo-9-(4-pyridylprop-1-yl)-9H-purin-6-ylamine;
2-(2-phenylethylthio)-8-bromo-9-(4-pyridylprop-1-yl)-9H-purin-6-ylamine;
2-(3-phenylpropylthio)-8-bromo-9-(4-pyridylprop-1-yl)-9H-purin-6-ylamine;
2-(2-phenylethylamino)-8-bromo-9-(4-piperidinbut-1-yl)-9H-purin-6-ylamine;
2-(3-phenylpropylamino)-8-bromo-9-(4-piperidinbut-1-yl)-9H-purin-6-ylamine;
2-(2-phenylethoxy)-8-bromo-9-(4-piperidinbut-1-yl)-9H-purin-6-ylamine;
2-(3-phenylpropoxy)-8-bromo-9-(4-piperidinbut-1-yl)-9H-purin-6-ylamine;
2-(2-phenylethylthio)-8-bromo-9-(4-piperidinbut-1-yl)-9H-purin-6-ylamine; and
2-(3-phenylpropylthio)-8-bromo-9-(4-piperidinbut-1-yl)-9H-purin-6-ylamine.

EXAMPLE 5

Preparation of a Compound of Formula I

A. Preparation of a Compound of Formula I Where $R^1$ is Phenyl, $R^2$ is Ethyl, $R^3$ is 2-Furyl, X is —NH—, and Y is Ethylene

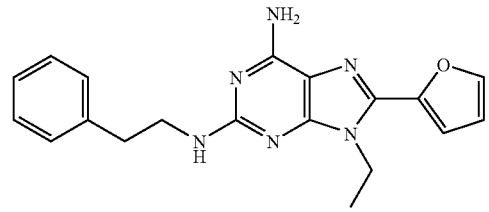

Formula I

A mixture of 2-(2-phenylethylamino)-8-bromo-9-ethyl-9H-purin-6-ylamine (0.28 mmol), tributylstannyl furan (440 μL, 1.4 mmol), and bis(triphenylphosphine)palladium dichloride (12 mg, 0.017 mmol) was dissolved in dry tetrahydrofuran (10 mL), and heated at 60° C. for 3 hours. The solvent was removed in vacuo, and the residue was partitioned between water and chloroform. The organic layer was dried ($Na_2SO_4$), filtered and concentrated in vacuo. The residue was dissolved in $CHCl_3$/MeOH and extracted with chloroform. The organic layers were dried over $Na_2SO_4$ and concentrated in vacuo. The residue was chromatographed on a silica gel column eluting with ethyl acetate/cyclohexane/methanol (60/36/4) to give 2-(2-phenylethylamino)-8-(furan-2-yl)-9-ethyl-9H-purin-6-ylamine as a chromatographically pure solid.

$^1$H NMR ($Me_2SO$-$d_6$) δ 1.33 (t, 3H, J=7.2 Hz, $CH_2CH_3$), 2.87 (t, 2H, J=7.3 Hz, $CH_2CH_2Ph$),), 3.49 (q, 2H, J=7.3 Hz, $CH_2CH_2Ph$), 4.30 (q, 2H, J=7.2 Hz, $CH_2CH_3$), 6.47 (bs, 1H, NH), 6.67 (m, 1H, H-Fur), 6.86 (s, 2H, $NH_2$), 6.99 (d, 1H, J=3.6 Hz, H-Fur), 7.29 (m, 5H, H-Ph), 7.91 (ps, 1H, H-Fur). Anal. ($C_{19}H_{20}N_6O$) C, H, N.

B. Preparation of a Compound of Formula I Where $R^2$ is Ethyl, X is —O—, Varying $R^1$, $R^3$, and Y Similarly, following the procedure of 5A above, but replacing 2-(2-phenylethylamino)-8-bromo-9-ethyl-9H-purin-6-ylamine by other compounds of formula (5) in which X is —O—, the following compounds of Formula I were prepared:

2-(2-phenylethoxy)-8-(furan-2-yl)-9-ethyl-9H-purin-6-ylamine;

$^1$H NMR ($Me_2SO$-$d_6$) δ 1.33 (t, 3H, J=7.0 Hz, $CH_2CH_3$), 3.03 (t, 2H, J=7.0 Hz, $CH_2CH_2Ph$), 4.35 (q, 2H, J=7.0 Hz, $CH_2CH_3$), 4.45 (t, 2H, J=7.0 Hz, $CH_2CH_2Ph$), 6.74 (m, 1H, H-Fur), 7.07 (d, 1H, J=3.6 Hz, H-Fur), 7.17–7.40 (m, 7H, H-Ph and $NH_2$), 7.95 (d, 1H, J=2.6 Hz, H-Fur). Anal. ($C_{19}H_{19}N_5O_2$) C, H, N.;

2-[(2-(4-methoxy)phenylethoxy]-8-(furan-2-yl)-9-ethyl-9H-purin-6-ylamine;

$^1$H NMR ($Me_2SO$-$d_6$) δ 1.33 (t, 3H, J=6.9 Hz, $CH_2CH_3$), 2.95 (t, 2H, J=6.9 Hz, $CH_2CH_2Ph$), 3.74 (s, 3H, $OCH_3$), 4.30–4.43 (m, 4H, $CH_2CH_3$ and $CH_2CH_2Ph$), 6.75 (m, 1H, H-Fur), 6.89 (d, 2H, J=8.5 Hz, H-Ph), 7.08 (d, 1H, J=3.3 Hz, H-Fur), 7.25 (d, 2H, J=8.5 Hz, H-Ph), 7.35 (s, 2H, NH$_2$), 7.95 (s, 1H, H-Fur). Anal. (C$_{20}$H$_{21}$N$_5$O$_3$) C, H, N.

2-(2-phenylethoxy)-8-(thien-2-yl)-9-ethyl-9H-purin-6-ylamine;

mp 162–165° C.; $^1$H NMR (Me$_2$SO-d$_6$) δ 1.35 (t, 3H, J=7.2 Hz, CH$_2$CH$_3$), 3.04 (t, 2H, J=7.0 Hz, CH$_2$CH$_2$Ph),), 4.35 (q, 2H, J=7.2 Hz, CH$_2$CH$_3$), 4.45 (t, 2H, J=7.0 Hz CH$_2$CH$_2$Ph), 7.23–7.35 (m, 8H, H-Ph, H-Thienyl, and NH$_2$), 7.63 (d, 1H, J=3.3 Hz, H-Thienyl), 7.76 (d, 1H, J=5.1 Hz, H-Thienyl). Anal. (C$_{19}$H$_{19}$N$_5$OS) C, H, N, S.

C. Preparation of a Compound of Formula I Where R$^1$ is Phenyl, R$^2$ is Ethyl, R$^3$ is 2-tetrahydrofuryl, X is —O—, and Y is Ethylene To a solution of 2-(2-phenylethoxy)-8-(furan-2-yl)-9-ethyl-9H-purin-6-ylamine (150 mg, 0.43 mmol) in 45 mL of isopropanol and 2 drops of concentrated HCl was added 150 mg of Pd(OH)$_2$, and the mixture was shaken with hydrogen at 170 psi and 65° C. for 7 hours. The catalyst was filtered off, washed with warm methanol, and the filtrate was concentrated to dryness. The residue was flash chromatographed on a silica gel column eluting with cyclohexane, -EtOAc-CH$_3$OH (60:33:7) to give 2-(2-phenylethoxy)-8-(tetrahydrofuran-2-yl)-9-ethyl-9H-purin-6-ylamine (71 mg, 47%) as chromatographically pure solid: mp 121–123° C.; $^1$H NMR (Me$_2$SO-d$_6$) δ 1.33 (t, 3H, J=7.1 Hz, CH$_2$CH$_3$), 1.87–2.30 (m, 3H, H-3-Fur and H-4-Fur), 2.55–2.75 (m, 1H, H-3-Fur), 3.02 (t, 2H, J=6.9 Hz, CH$_2$CH$_2$Ph), 3.83 (m, 2H, H-5-Fur), 4.15 (q, 2H, J=7.1 Hz, CH$_2$CH$_3$), 4.41 (t, 2H, J=6.9 Hz, CH$_2$CH$_2$Ph), 5.14 (t, 1H, J=6.6 Hz, H-2-Fur), 7.17–7.40 (m, 7H, H-Ph and NH$_2$). Anal. (C$_{19}$H$_{23}$N$_5$O$_2$) C, H, N.

D. Preparation of a Compound of Formula I Where R$^1$ is Phenyl, R$^2$ is Ethyl, R$^3$ is Ethoxy, X is —O—, and Y is Ethylene To a suspension of 2-(2-phenylethoxy)-8-bromo-9-ethyl-9H-purin-6-ylamine (145 mg, 0.4 mmol) and dry NaOH (80 mg, 2.0 mmol) was added ethanol (25 mL). This mixture was heated at 85° C. for 7 hours. The solvent was removed under reduced pressure and the residue was neutralized with 2N HCl and extracted with CHCl$_3$. The organic layer was dried (Na$_2$SO$_4$) and concentrated in vacuo. The residue was recrystallized from acetonitrile to give 2-(2-phenylethoxy)-8-ethoxy-9-ethyl-9H-purin-6-ylamine (68 mg, 52%) as a white solid: mp 161–164° C.; $^1$H NMR (Me$_2$SO-d$_6$) δ 1.26 (t, 3H, J=7.1 Hz, OCH$_2$CH$_3$), 1.33 (t, 3H, J=7.0 Hz, NCH$_2$CH$_3$), 3.00 (t, 2H, J=6.9 Hz, CH$_2$CH$_2$Ph), 3.88 (q, 2H, J=7.1 Hz, OCH$_2$CH$_3$), 4.38 (t, 2H, J=6.9 Hz, CH$_2$CH$_2$Ph), 4.48 (q, 2H, J=7.0 Hz, NCH$_2$CH$_3$), 6.79 (s, 2H, NH$_2$), 7.18–7.36 (m, 5H, H-Ph). Anal. (C$_{17}$H$_{21}$N$_5$O$_2$) C, H, N.

E. Preparation of a Compound of Formula I, Varying R$^1$, R$^2$, X, and Y

Similarly, following the procedure of 5A, 5B, or 5C above, the following compounds of formula (5) are prepared:

2-(2-benzylamino)-8-(furan-2-yl)-9-methyl-9H-purin-6-ylamine;
2-(3-phenylpropylamino)-8-(thien-2-yl)-9-methyl-9H-purin-6-ylamine;
2-(2-phenylmethoxy)-8-(tetrahydrofuran-2-yl)-9-methyl-9H-purin-6-ylamine;
2-(3-phenylpropoxy)-8-phenyl-9-methyl-9H-purin-6-ylamine;
2-(2-phenylethylthio)-8-(pyrid-2-yl)-9-methyl-9H-purin-6-ylamine;
2-(3-phenylpropylthio)-8-(2-methylfuran-3-yl)-9-methyl-9H-purin-6-ylamine;
2-(2-phenylethylamino)-8-(furan-2-yl)-9-n-propyl-9H-purin-6-ylamine;
2-(3-phenylpropylamino)-8-(thien-2-yl)-9-n-propyl-9H-purin-6-ylamine;
2-(2-phenylethoxy)-8-(tetrahydrofuran-2-yl)-9-n-propyl-9H-purin-6-ylamine;
2-(3-phenylpropoxy)-8-(4-methoxyphenyl)-9-n-propyl-9H-purin-6-ylamine;
2-(2-phenylethylthio)-8-(4-fluoropyrid-4-yl)-9-n-propyl-9H-purin-6-ylamine;
2-(3-phenylpropylthio)-8-(2-trifluoromethylfuran)-9-n-propyl-9H-purin-6-ylamine;
2-(2-phenylethylamino)-8-(furan-2-yl)-9-isobutyl-9H-purin-6-ylamine;
2-(3-phenylpropylamino)-8-(furan-2-yl)-9-isobutyl-9H-purin-6-ylamine;
2-(2-phenylethoxy)-8-(furan-2-yl)-9-isobutyl-9H-purin-6-ylamine;
2-(3-phenylpropoxy)-8-(furan-2-yl)-9-isobutyl-9H-purin-6-ylamine;
2-(2-phenylethylthio)-8-(furan-2-yl)-9-isobutyl-9H-purin-6-ylamine;
2-(3-phenylpropylthio)-8-(furan-2-yl)-9-isobutyl-9H-purin-6-ylamine;
2-(2-phenylethylamino)-8-(furan-2-yl)-9-(2-fluoropropyl)-9H-purin-6-ylamine;
2-(3-phenylpropylamino)-8-(furan-2-yl)-9-(2-fluoropropyl)-9H-purin-6-ylamine;
2-(2-phenylethoxy)-8-(furan-2-yl)-9-(2-fluoropropyl)-9H-purin-6-ylamine;
2-(3-phenylpropoxy)-8-(furan-2-yl)-9-(2-fluoropropyl)-9H-purin-6-ylamine;
2-(2-phenylethylthio)-8-(furan-2-yl)-9-(2-fluoropropyl)-9H-purin-6-ylamine;
2-(3-phenylpropylthio)-8-(furan-2-yl)-9-(2-fluoropropyl)-9H-purin-6-ylamine;
2-(2-phenylethylamino)-8-(furan-2-yl)-9-(n-pentyl)-9H-purin-6-ylamine;
2-(3-phenylpropylamino)-8-(furan-2-yl)-9-(n-pentyl)-9H-purin-6-ylamine;
2-(2-phenylethoxy)-8-(furan-2-yl)-9-(n-pentyl)-9H-purin-6-ylamine;
2-(3-phenylpropoxy)-8-(furan-2-yl)-9-(n-pentyl)-9H-purin-6-ylamine;
2-(2-phenylethylthio)-8-(furan-2-yl)-9-(n-pentyl)-9H-purin-6-ylamine;
2-(3-phenylpropylthio)-8-(furan-2-yl)-9-(n-pentyl)-9H-purin-6-ylamine;
2-(2-phenylethylamino)-8-(furan-2-yl)-9-(n-decyl)-9H-purin-6-ylamine;
2-(3-phenylpropylamino)-8-(furan-2-yl)-9-(n-decyl)-9H-purin-6-ylamine;
2-(2-phenylethoxy)-8-(furan-2-yl)-9-(n-decyl)-9H-purin-6-ylamine;
2-(3-phenylpropoxy)-8-(furan-2-yl)-9-(n-decyl)-9H-purin-6-ylamine;
2-(2-phenylethylthio)-8-(furan-2-yl)-9-(n-decyl)-9H-purin-6-ylamine;
2-(3-phenylpropylthio)-8-(furan-2-yl)-9-(n-decyl)-9H-purin-6-ylamine;
2-(2-phenylethylamino)-8-(furan-2-yl)-9-allyl-9H-purin-6-ylamine;
2-(3-phenylpropylamino)-8-(furan-2-yl)-9-allyl-9H-purin-6-ylamine;

2-(2-phenylethoxy)-8-(furan-2-yl)-9-allyl-9H-purin-6-ylamine;
2-(3-phenylpropoxy)-8-(furan-2-yl)-9-allyl-9H-purin-6-ylamine;
2-(2-phenylethylthio)-8-(furan-2-yl)-9-allyl-9H-purin-6-ylamine;
2-(3-phenylpropylthio)-8-(furan-2-yl)-9-allyl-9H-purin-6-ylamine;
2-(2-phenylethylamino)-8-(furan-2-yl)-9-(hept-4-enyl)-9H-purin-6-ylamine;
2-(3-phenylpropylamino)-8-(furan-2-yl)-9-(hept-4-enyl)-9H-purin-6-ylamine;
2-(2-phenylethoxy)-8-(furan-2-yl)-9-(hept-4-enyl)-9H-purin-6-ylamine;
2-(3-phenylpropoxy)-8-(furan-2-yl)-9-(hept-4-enyl)-9H-purin-6-ylamine;
2-(2-phenylethylthio)-8-(furan-2-yl)-9-(hept-4-enyl)-9H-purin-6-ylamine;
2-(3-phenylpropylthio)-8-(furan-2-yl)-9-(hept-4-enyl)-9H-purin-6-ylamine;
2-(2-phenylethylamino)-8-(furan-2-yl)-9-(prop-2-ynyl)-9H-purin-6-ylamine;
2-(3-phenylpropylamino)-8-(furan-2-yl)-9-(prop-2-ynyl)-9H-purin-6-ylamine;
2-(2-phenylethoxy)-8-(furan-2-yl)-9-(prop-2-ynyl)-9H-purin-6-ylamine;
2-(3-phenylpropoxy)-8-(furan-2-yl)-9-(prop-2-ynyl)-9H-purin-6-ylamine;
2-(2-phenylethylthio)-8-(furan-2-yl)-9-(prop-2-ynyl)-9H-purin-6-ylamine;
2-(3-phenylpropylthio)-8-(furan-2-yl)-9-(prop-2-ynyl)-9H-purin-6-ylamine;
2-(2-phenylethylamino)-8-(furan-2-yl)-9-cyclohexylmethyl-9H-purin-6-ylamine;
2-(3-phenylpropylamino)-8-(furan-2-yl)-9-cyclohexylmethyl-9H-purin-6-ylamine;
2-(2-phenylethoxy)-8-(furan-2-yl)-9-cyclohexylmethyl-9H-purin-6-ylamine;
2-(3-phenylpropoxy)-8-(furan-2-yl)-9-cyclohexylmethyl-9H-purin-6-ylamine;
2-(2-phenylethylthio)-8-(furan-2-yl)-9-cyclohexylmethyl-9H-purin-6-ylamine;
2-(3-phenylpropylthio)-8-(furan-2-yl)-9-cyclohexylmethyl-9H-purin-6-ylamine;
2-(2-phenylethylamino)-8-(furan-2-yl)-9-phenylethyl-9H-purin-6-ylamine;
2-(3-phenylpropylamino)-8-(furan-2-yl)-9-phenylethyl-9H-purin-6-ylamine;
2-(2-phenylethoxy)-8-(furan-2-yl)-9-phenylethyl-9H-purin-6-ylamine;
2-(3-phenylpropoxy)-8-(furan-2-yl)-9-phenylethyl-9H-purin-6-ylamine;
2-(2-phenylethylthio)-8-(furan-2-yl)-9-phenylethyl-9H-purin-6-ylamine;
2-(3-phenylpropylthio)-8-(furan-2-yl)-9-phenylethyl-9H-purin-6-ylamine;
2-(2-phenylethylamino)-8-(furan-2-yl)-9-(4-methoxyphenyl)ethyl-9H-purin-6-ylamine;
2-(3-phenylpropylamino)-8-(furan-2-yl)-9-(4-methoxyphenyl)ethyl-9H-purin-6-ylamine;
2-(2-phenylethoxy)-8-(furan-2-yl)-9-(4-methoxyphenyl)ethyl-9H-purin-6-ylamine;
2-(3-phenylpropoxy)-8-(furan-2-yl)-9-(4-methoxyphenyl)ethyl-9H-purin-6-ylamine;
2-(2-phenylethylthio)-8-(furan-2-yl)-9-(4-methoxyphenyl)ethyl-9H-purin-6-ylamine;
2-(3-phenylpropylthio)-8-(furan-2-yl)-9-(4-methoxyphenyl)ethyl-9H-purin-6-ylamine;
2-(2-phenylethylamino)-8-(furan-2-yl)-9-(4-pyridylprop-1-yl)-9H-purin-6-ylamine;
2-(3-phenylpropylamino)-8-(furan-2-yl)-9-(4-pyridylprop-1-yl)-9H-purin-6-ylamine;
2-(2-phenylethoxy)-8-(furan-2-yl)-9-(4-pyridylprop-1-yl)-9H-purin-6-ylamine;
2-(3-phenylpropoxy)-8-(furan-2-yl)-9-(4-pyridylprop-1-yl)-9H-purin-6-ylamine;
2-(2-phenylethylthio)-8-(furan-2-yl)-9-(4-pyridylprop-1-yl)-9H-purin-6-ylamine;
2-(3-phenylpropylthio)-8-(furan-2-yl)-9-(4-pyridylprop-1-yl)-9H-purin-6-ylamine;
2-(2-phenylethylamino)-8-(furan-2-yl)-9-(4-piperidinbut-1-yl)-9H-purin-6-ylamine;
2-(3-phenylpropylamino)-8-(furan-2-yl)-9-(4-piperidinbut-1-yl)-9H-purin-6-ylamine;
2-(2-phenylethoxy)-8-(furan-2-yl)-9-(4-piperidinbut-1-yl)-9H-purin-6-ylamine;
2-(3-phenylpropoxy)-8-(furan-2-yl)-9-(4-piperidinbut-1-yl)-9H-purin-6-ylamine;
2-(2-phenylethylthio)-8-(furan-2-yl)-9-(4-piperidinbut-1-yl)-9H-purin-6-ylamine; and
2-(3-phenylpropylthio)-8-(furan-2-yl)-9-(4-piperidinbut-1-yl)-9H-purin-6-ylamine.

EXAMPLE 6

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

EXAMPLE 7

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 8

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

EXAMPLE 9

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 10

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 11

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 12

A subcutaneous formulation may be prepared as follows:

| Ingredient | Quantity |
| --- | --- |
| Active Ingredient | 5.0 mg |
| Corn Oil | 1.0 mL |

EXAMPLE 13

An injectable preparation is prepared having the following composition:

| Ingredients | Amount |
| --- | --- |
| Active ingredient | 2.0 mg/ml |
| Mannitol, USP | 50 mg/ml |
| Gluconic acid, USP | q.s. (pH 5–6) |
| water (distilled, sterile) | q.s. to 1.0 ml |
| Nitrogen Gas, NF | q.s. |

EXAMPLE 14

A topical preparation is prepared having the following composition:

| Ingredients | grams |
| --- | --- |
| Active ingredient | 0.2–10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 15

Sustained Release Composition

| Ingredient | Weight Range (%) | Preferred Range (%) | Most Preferred |
|---|---|---|---|
| Active ingredient | 50–95 | 70–90 | 75 |
| Microcrystalline cellulose (filler) | 1–35 | 5–15 | 10.6 |
| Methacrylic acid copolymer | 1–35 | 5–12.5 | 10.0 |
| Sodium hydroxide | 0.1–1.0 | 0.2–0.6 | 0.4 |
| Hydroxypropyl methylcellulose | 0.5–5.0 | 1–3 | 2.0 |
| Magnesium stearate | 0.5–5.0 | 1–3 | 2.0 |

The sustained release formulations of this invention are prepared as follows: compound and pH-dependent binder and any optional excipients are intimately mixed(dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl. methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400–600 mg, 650–850 mg, and 900–1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 16

$A_{2A}$ Binding Assays

Reagents: A tritiated adenosine $A_{2A}$ antagonist, 4-(2-[7-amino-2-(2-furyl)[1,2,4]-triazolo[2,3-a][1,3,5]triazin-5-ylamino]ethyl)phenol ($^3$H-ZM-241385), the adenosine deaminase inhibitor erythro-9-(2-hydroxy-3-nonyl)adenine (EHNA), the adenosine kinase inhibitor iodotubercidin, and forskolin were purchased from Research Biochemicals (Natick, Mass.). Concentrated stock solution (10–100 mM) of forskolin as dissolved in dimethylsulfoxide, stored as aliquots at −80° C., and diluted in physiological saline for use in experiments. The final content of dimethylsulfoxide in saline during experiments was not more than 0.1%.

Binding Assays

Membranes containing $A_{2A}$-adenosine receptors for use in radioligand binding assays were prepared from cells from the guinea pig cerebral cortex. Briefly, freshly-isolated guinea pig brain cortical tissue was homogenized in ice-cold 50 mM Tris-HCl buffer (pH 7.4) using six up and down strokes of an ice-chilled Potter-Elvejhem tissue grinder and a motor-driven teflon™ pestle. A crude membrane preparation was isolated by centrifugation of the homogenate at 15,000 g for 20 min at 4° C. The membrane pellet was resuspended in fresh Tris buffer and pelleted again by centrifugation. The final membrane pellet was suspended in Tris buffer to achieve a protein content of 1.1–1.4 mg/ml and divided into aliquots for storage at −80° C. until needed for assays and 5 U/ml adenosine deaminase, and stored as aliquots in liquid nitrogen until needed for assays.

The binding assays utilized 0.2 mg of pig striatal membranes that had been treated with adenosine deaminase and 50 mM Tris buffer (pH=7.4) followed by mixing. 2 μL of serially diluted DMSO stock solution of the compounds of this invention at concentrations ranging from 100 μM to 10 nM or the control received 2 μL of DMSO alone, then the tritiated antagonist 4-(2-[7-amino-2-(2 furyl)[[1,2,4]-triazol [2,33a][1,3,5]triazin-amino]ethyl)phenol ($^3$H-ZM 241385) in Tris buffer (50 mM, pH of 7.4) was added to achieve a final concentration of 2 nM. After incubation at 23° C. for 2 hours, the solutions were filtered using a membrane harvester with multiple washing of the membranes (3×). The filter disks were counted in scintillation cocktail affording the amount of displacement 3H-ZM241385 by the competitive binding compositions of this invention. Radioligand binding data was analyzed using GraphPad Prism version 2.01 (San Diego, Calif.). When appropriate, the significance of differences among 3 or more individual mean values was determined by one-way way ANOVA followed by Student-Newman-Keuls test. A P value less than 0.05 was considered to indicate a statistically significant difference.

Similarly, the binding of the compounds of the invention to adenosine $A_1$ and $A_3$ adenosine receptors is determined utilizing competive binding assays using tritiated N-cyclopentyladenosine ($^3$H-CPA) or tritiated 4-aminobenzy-5'-N-methylcarboxamido-adenosine ($^3$HABMECA) respectively in place of $^3$H-ZM-241385.

The results obtained from the above examples indicate that the compounds of the invention are $A_{2A}$ antagonists, and consequently useful for the treatment of cardiovascular disorders and CNS diseases including Parkinson's disease.

EXAMPLE 17

Evaluation of Anti-Parkinsonian Activity in vivo Haloperidol-induced Catalepsy in the Rat This method assesses the ability of an animal to respond to an externally imposed posture after receiving the neuroleptic dopamine D2 antagonist haloperidol. Drugs which are effective in treating Parkinson's disease, such as L-DOPA, block haloperidol-induced catalepsy (Mandhane, S. N.;

Chopde, C. T.; Ghosh, A. K. (1997). Adenosine $A_{2A}$ receptors modulate haloperidol-induced catalepsy in rats.

The compounds of the invention are prepared in injectable form and diluted to a final concentration using physiological saline. 3,7-Dimethyl-1-propargylxanthine (DMPX) (0, 3 mg/kg) is dissolved in saline. All drugs are administered in a volume of 2 ml/kg. Animals receive three injections: (1) vehicle or compound p.o. 6 hours prior to testing, (2) haloperidol (0.2 mg/kg) i.p. 2.5 hours prior to testing, and (3) vehicle or DMPX (3 mg/kg) 30 minutes prior to testing.

The test procedure is as follows:

Step I The rat is taken out of the home cage and placed on a table. If the rat failed to move when touched gently on the back or pushed, a score of 0.5 is assigned.

Step II The front paws of the rat are placed alternately on a 3 cm high wooden block. If the rat fails to correct this posture within 15 seconds, a score of 0.5 for each paw is added to the score of Step I.

Step III The front paws of the rat are placed alternately on a 9 cm high wooden block. If the rat fails to correct the posture within 15 seconds, a score is added to the scores of Step I and II. Thus, for any animal, the highest score obtainable is 3.5 (cut-off score) reflecting total catalepsy.

Data from the experiment are analysed using Kruskal-Wallis ANOVA followed by Mann-Whitney U test when appropriate, and are expressed as means +/− standard error of the mean $*p<0.05$ versus vehicle control.

MPTP Lesion Model

Mice (C57/BL Harlan) receive a unilateral intrastriatal injection of the test compound, vehicle control, and positive control, in a volume of 1.0 .mu·l (15 mice per group). 30 min. after administration of the test compound all mice are systemically administered MPTP (N-methyl-4-phenyl-1,2,5,6-tetrahydropyridine) (25 mg/kg s.c), and this MPTP treatment is repeated 24 hours later. At suitable time points the spontaneous locomotor activity of the animals, as measured in automated activity monitors, is compared with control animals. Animals are sacrificed 14 days after the second MPTP injection and striatal tissue is dissected out for HPLC analysis of dopamine and its metabolites, 3,4-dihydroxyphenylacetic acid and homovanillic acid. Reverse-phase HPLC in conjunction with electrochemical detection (Antec Decade detector, glossy carbon cell, set to +0.65 V versus a Ag/AgCl reference) is employed. The HPLC mobile phase consisted of 0.15 M NaH.sub.2 PO.sub.4, 0.1 mM EDTA, 0.55 mM octyl sulphate, 16% methanol (pH 3.6, adjusted with orthophosphoric acid). The effects of test compounds on MPTP-induced mesencephalic damage is demonstrated by comparison with dopamine, 3,4-dihydroxyphenylacetic acid and homovanillic acid levels in caudate tissue taken ipsilateral and controlateral to the test compound injection. The influence of test compounds on MPTP-induced effects on locomotion and catecholamine and metabolite tissue levels is assessed by repeated measures analysis of variance (ANOVA) with appropriate tests.

EXAMPLE 18

Determination of $A_{2A}$ Antagonist Activity

Cell Culture

CHO cells (Chinese hamster ovary cells) are grown in petri dishes using Dulbecco's Modified Eagle's Medium (DMEM) containing 2.5 μg ml$^{-1}$ amphotericin B, 100 U ml$^{-1}$ penicillin G, 0.1 mg ml$^{-1}$ streptomycin sulfate and 5% fetal bovine serum in a humidified atmosphere of 95% air and 5% $CO_2$. Cells are subcultured twice weekly by dispersion in Hank's Balanced Salt Solution (HBSS) without the divalent cations and containing 1 mM EDTA with experiments being performed at approximately one day preconfluence.

Membrane Preparations

Attached cells are washed twice with HBSS (2×10 ml), scraped free of the plate with the aid of a rubber policeman in 5 ml of 50 mM Tris-HCl buffer pH 7.4 at 4° C. and the suspension homogenized for 10 seconds. The suspension is then centrifuged at 27,000×g for 10 min. The pellet is resuspended in homogenization buffer by vortexing and centrifuged as described above. The final pellet is resuspended in 1 vol of 50 mM Tris-HCl buffer pH 7.4 containing 5 mM $MgCl_2$ for binding assays. For the [$^{35}$S]GTP□S binding assay the final pellet is resuspended in 50 mM Tris-HCl pH 7.4 containing 5 mM $MgCl_2$, 100 mM NaCl and 1 mM dithiothreitol. This membrane suspension is then placed in liquid nitrogen for 10 min, thawed and used for assays. The protein content is determined with a Bradford™ Assay Kit using bovine serum albumin as standard.

[$^{35}$S]GTPS Binding Assays

The ability of the adenosine $A_{2A}$-antagonists to stimulate [$^{35}$S] GTPS binding is determined by a modification of the method described by Lorenzen et al. (1996 Mol. Pharmacol. 49:915). Briefly, membranes isolated from CHO cells (30–50 μg) are incubated in a volume of 0.1 ml containing 50 mM Tris-HCl buffer pH 7.4, 5 mM $MgCl_2$, 100 mM NaCl, 1 mM dithiothreitol, 0.2 units ml$^{-1}$ adenosine deaminase, 0.5% BSA, 1 mM EDTA, 10 mM GDP, and 0.3 nM [$^{35}$S]GTPS. Various concentrations of an $A_{2A}$ agonist, CGS21680, are added and. The ability of the putative $A_{2A}$ antagonists to block the stimulation [$^{35}$S]GTPS binding produced by CGS21680 is determined by adding varying concentrations of the compounds to the assay mixture. The cells are incubated for 90 min at 30° C. At the end of the incubation, each suspension is filtered and the retained radioactivity determined.

cAMP Assay

The ability of the putative $A_{2A}$ antagonist to inhibit CGS21680 stimulated cAMP accumulation is determined by culturing CHO cells in clear bottomed 96 well microtiter plates at concentrations between $10^4$ to $10^6$ cells per well in 40 ul of HBSS at 37° C. (5% $CO_2$ and 95% humidity). At the beginning of the experiment fresh media containing rolipram (50 uM) and various concentrations CGS21680. Then, various concentrations of the putative adenosine $A_{2A}$ receptor antagonists are added and the cells cultured for 10 min at 37° C. The cells are immediately lysed by treatment 5 ul of 10% dodecyltrimethylammonium bromide followed by shaking using microplate shaker.

The cAMP content of the supernatant is determined by modification of a radioimmunoassay method described by Harper and Brooker (1975. J. Cyclic nucleotide Res 1:207). Briefly, an aliquot of the supernatant (0.01 mL) is mixed with 0.04 mL of HBSS, 0.05 mL of 50 mmol/L sodium acetate buffer (pH 6.2) containing 10 mmol/L $CaCl_2$, [$^{125}$I] ScAMP-TME (12500 dpm), and 0.05 mL of anti-cAMP antibody (1:2000 dilution with 0.1% bovine serum albumin in distilled water). The samples were then incubated at 4° C. for 16 hours. At the end of the incubation, 70 μL of a 50% (wt/vol) hydroxyapatite suspension is added to each tube. The suspensions were gently agitated and then incubated for 10 minutes at 4° C. Antibody-bound radioactivity adsorbed to hydroxyapatite is collected onto glass fiber filters by vacuum filtration using a Brandel cell harvester. Radioactivity retained by the filter is counted in a gamma counter. The results are expressed as the total [$^{125}$I]ScAMP bound minus the amount of nonspecific ([$^{125}$I]ScAMP-TME bound (i.e. amount of [$^{125}$I]ScAMP bound in the presence of 3 μmol/L unlabeled cAMP).

The invention claimed is:

1. A compound of the Formula I:

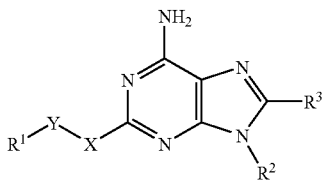

Formula I wherein:
- $R^1$ is optionally substituted ary or optionally substituted heteroaryl;
- $R^2$ is optionally substituted lower alkyl;
- $R^3$ is halogen, optionally substituted alkoxy, optionally substituted aryl, optionally substituted heteroaryl, or optionally substituted heterocyclyl;
- X is —O—, —S—, or —NH—; and
- Y is optionally substituted alkylene;

with the provisos that
- a. $R^3$ cannot be optionally substituted pyrazolyl or optionally substituted furanyl;
- b. when X is —NH— and Y is —CH$_2$—, $R^1$ is not dihydroxyphenyl; and
- c. $R^2$ cannot be optionally substituted benzyl when $R^3$ is hydrogen.

2. The compound of claim 1, wherein $R^1$ is optionally substituted aryl.

3. The compound of claim 2, wherein $R^3$ is halogen, or optionally substituted heteroaryl.

4. The compound of claim 3, wherein Y is lower alkylene.

5. The compound of claim 4, wherein X is —NH—.

6. The compound of claim 5, wherein $R^2$ is methyl, ethyl, or n-propyl.

7. The compound of claim 6, wherein $R^1$ phenyl, $R^2$ is ethyl, $R^3$ is bromo, and Y is methylene, namely 2-benzylamino-8-bromo-9-ethyl-9H-purin-6-ylamine.

8. The compound of claim 6, wherein $R^1$ is phenyl, $R^2$ is ethyl, $R^3$ is bromo, and Y is ethylene, namely 2-(2-phenylethyl)amino-8-bromo-9-ethyl-9H-purin-6-ylamine.

9. The compound of claim 6, wherein $R^1$ is 3,4-dimethoxyphenyl, $R^2$ is ethyl, $R^3$ is bromo, and Y is ethylene, namely 2-[2-(3,4-dimethoxyphenyl)ethyl]amino-8-bromo-9-ethyl-9H-purin-6-ylamine.

10. The compound of claim 6, wherein $R^1$ is 3,4-dihydroxyphenyl, $R^2$ is ethyl, $R^3$ is bromo, and Y is ethylene, namely 2-[2-(3,4-dihydroxyphenyl)ethyl]amino-8-bromo-9-ethyl-9H-purin-6-ylamine.

11. The compound of claim 6, wherein $R^1$ is 4-bromophenyl, $R^2$ is ethyl, $R^3$ is bromo, and Y is ethylene, namely 2-[2-(4-bromophenyl)ethyl]amino-8-bromo-9-ethyl-9H-purin-6-ylamine.

12. The compound of claim 6, wherein $R^1$ is 4-fluorophenyl, $R^2$ is ethyl, $R^3$ is bromo, and Y is ethylene, namely 2-[2-(4-fluorophenyl)ethyl]amino-8-bromo-9-ethyl-9H-purin-6-ylamine.

13. The compound of claim 6, wherein $R^1$ is 4-hydroxyphenyl, $R^2$ is ethyl, $R^3$ is bromo, and Y is ethylene, namely 2-[2-(4-hydroxyphenyl)ethyl]amino-8-bromo-9-ethyl-9H-purin-6-ylamine.

14. The compound of claim 6, wherein $R^1$ is 4-methoxyphenyl, $R^2$ is ethyl, $R^3$ is bromo, and Y is ethylene, namely 2-[2-(4-methoxyphenyl)ethyl]amino-8-bromo-9-ethyl-9H-purin-6-ylamine.

15. The compound of claim 4, wherein X is —O—.

16. The compound of claim 15, wherein $R^2$ is methyl, ethyl, or n-propyl.

17. The compound of claim 16, wherein $R^1$ is phenyl, $R^2$ is ethyl, $R^3$ is bromo, and Y is ethylene, namely 2-(2-phenylethoxy)-8-bromo-9-ethyl-9H-purin-6-ylamine.

18. The compound of claim 4, wherein X is —S—.

19. The compound of claim 18, wherein $R^2$ is methyl, ethyl, or n-propyl.

20. The compound of claim 19, wherein $R^1$ is phenyl, $R^2$ is ethyl, $R^3$ is bromo, and Y is ethylene, namely 2-(2-phenylethylthio)-8-bromo-9-ethyl-9H-purin-6-ylamine.

21. A pharmaceutical composition comprising at least one pharmaceutically acceptable excipient and a therapeutically effective amount of a compound of claim 1.

* * * * *